(12) United States Patent
Yamada et al.

(10) Patent No.: US 9,067,065 B2
(45) Date of Patent: Jun. 30, 2015

(54) PARTICLE BEAM IRRADIATION APPARATUS AND PARTICLE BEAM THERAPY SYSTEM UTILIZING A BEAM POSITION MONITOR TO PROVIDE FEEDBACK ADJUSTMENTS BASED ON THE BEAM POSITION

(75) Inventors: Yukiko Yamada, Chiyoda-ku (JP);
Hisashi Harada, Chiyoda-ku (JP);
Takaaki Iwata, Chiyoda-ku (JP);
Toshihiro Otani, Chiyoda-ku (JP);
Masahiro Ikeda, Chiyoda-ku (JP);
Kazushi Hanakawa, Chiyoda-ku (JP);
Taizo Honda, Chiyoda-ku (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 13/977,058

(22) PCT Filed: Mar. 7, 2011

(86) PCT No.: PCT/JP2011/055235
§ 371 (c)(1),
(2), (4) Date: Jun. 28, 2013

(87) PCT Pub. No.: WO2012/120615
PCT Pub. Date: Sep. 13, 2012

(65) Prior Publication Data
US 2013/0274538 A1    Oct. 17, 2013

(51) Int. Cl.
*A61N 5/10* (2006.01)
*G21K 1/093* (2006.01)

(52) U.S. Cl.
CPC ............ *A61N 5/1048* (2013.01); *A61N 5/1043* (2013.01); *A61N 5/1075* (2013.01); *A61N 2005/1087* (2013.01); *G21K 1/093* (2013.01)

(58) Field of Classification Search
CPC . A61N 5/1042; A61N 5/1004; A61N 5/1049; A61N 5/4065; A61N 5/1067; A61N 5/1075

USPC ........................................................ 250/492.1
See application file for complete search history.

(56) References Cited

U.S. PATENT DOCUMENTS

| 5,426,356 A * | 6/1995 | Matsuura et al. .............. 318/578 |
| 6,717,162 B1 * | 4/2004 | Jongen ........................ 250/505.1 |

(Continued)

FOREIGN PATENT DOCUMENTS

| JP | 2005-296162 A | 10/2005 |
| JP | 2007-061438 a | 3/2007 |

(Continued)

OTHER PUBLICATIONS

International Search Report (PCT/ISA/210) issued on Jun. 14, 2011, by the Japanese Patent Office as the International Searching Authority for International Application No. PCT/JP2011/055235.
(Continued)

*Primary Examiner* — Phillip A Johnston
*Assistant Examiner* — Sean Luck
(74) *Attorney, Agent, or Firm* — Buchanan Ingersool & Rooney PC

(57) ABSTRACT

The particle beam irradiation apparatus comprises: a position monitor that detects a passing position of a charged particle beam; and an irradiation control apparatus that calculates a distance from a predetermined reference point to the position monitor, calculates a beam irradiation position on an irradiation subject, and controls irradiation of the beam; wherein the irradiation control apparatus includes a position calculation apparatus that calculates the beam irradiation position, based on a beam position detected by the position monitor, a scanning starting point distance information on a distance from a irradiation plane of the irradiation subject to a scanning starting point, of the beam, in a scanning electromagnet, and a position monitor distance information on a distance, from the irradiation plane to the position monitor, that is calculated based on the calculated distance.

8 Claims, 11 Drawing Sheets

(56) References Cited

U.S. PATENT DOCUMENTS

| | | | |
|---|---|---|---|
| 6,774,383 B2 * | 8/2004 | Norimine et al. | 250/505.1 |
| 6,780,149 B1 * | 8/2004 | Schulte | 600/1 |
| 6,891,177 B1 * | 5/2005 | Kraft et al. | 250/505.1 |
| 7,060,997 B2 * | 6/2006 | Norimine et al. | 250/505.1 |
| 7,193,227 B2 * | 3/2007 | Hiramoto et al. | 250/492.3 |
| 7,262,424 B2 * | 8/2007 | Moriyama et al. | 250/492.3 |
| 7,402,819 B2 * | 7/2008 | Saracen | 250/492.1 |
| 7,657,301 B2 * | 2/2010 | Mate et al. | 600/424 |
| 8,314,411 B2 | 11/2012 | Harada et al. | |
| 2003/0141460 A1 * | 7/2003 | Kraft | 250/492.1 |
| 2007/0053492 A1 * | 3/2007 | Kidani et al. | 378/65 |
| 2007/0295817 A1 * | 12/2007 | Massieu et al. | 235/462.23 |
| 2007/0295910 A1 * | 12/2007 | Harada | 250/354.1 |
| 2009/0039256 A1 * | 2/2009 | Fujii et al. | 250/306 |
| 2009/0189092 A1 * | 7/2009 | Aoi et al. | 250/492.1 |
| 2011/0218429 A1 | 9/2011 | Harada et al. | |

FOREIGN PATENT DOCUMENTS

| | | | |
|---|---|---|---|
| JP | 2009-000347 A | | 1/2009 |
| JP | 4393581 B1 | | 1/2010 |
| JP | 4393581 | * | 6/2010 |
| JP | 2010-284507 A | | 12/2010 |
| WO | 2010/122662 A1 | | 10/2010 |

OTHER PUBLICATIONS

Office Action issued on Oct. 9, 2013, by the Taiwanese Patent Office in corresponding Taiwanese Patent Application No. 100140843, and an English Translation of the Office Action. (9 pages).

Office Action (Reason) issued on Apr. 8, 2014, by the Japanese Patent Office in corresponding Japanese Patent Application No. 2013-503257, and an English Translation of the Office Action. (5 pages).

Extended European Search Report issued Jul. 29, 2014, by the European Patent Office in corresponding European Patent Application No. 11860386.9-1652. (6 pages).

* cited by examiner

PARTICLE BEAM IRRADIATION APPARATUS AND PARTICLE BEAM THERAPY SYSTEM UTILIZING A BEAM POSITION MONITOR TO PROVIDE FEEDBACK ADJUSTMENTS BASED ON THE BEAM POSITION

TECHNICAL FIELD

The present invention relates to a particle beam irradiation apparatus and a particle beam therapy system for performing treatment of a cancer or the like by use of a particle beam.

BACKGROUND ART

Irradiation methods in particle beam therapy systems mainly include a broad irradiation method in which a charged particle beam is enlarged in a dispersion manner by a scatterer, the shape of the enlarged charged particle beam is made to coincide with the shape of an irradiation subject in order to form an irradiation field, and then the beam is irradiated all at once onto the whole diseased site of a patient as an irradiation subject; and a scanning irradiation method (the spot-scanning method, the raster-scanning method, and the like) in which a thin, a pencil-like beam is irradiated by scanning the beam with a scanning electromagnet in such a way that the scanning area coincides with the shape of an irradiation subject.

In recent years, in order to treat a complex-shape diseased site, the demand for the degree of freedom in forming a beam has become large. A brain tumor is an example of these diseased sites. Because being surrounded by major organs onto which any beam should not be irradiated, a brain tumor has a complex shape. The broad irradiation method is not suitable for the treatment of this kind of diseased site. The reason for that is as follows. In the broad irradiation method, a beam is spread in the three dimensions, and the unnecessary part thereof is eliminated by use of a collimator or a bolus; then, an irradiation field is formed in such a way as to coincide with the shape of a diseased site. In the broad irradiation method, in the case where a complex-shape diseased site is treated, it is difficult to form a complex-shape irradiation field only with one-time irradiation. Therefore, a method should be utilized in which irradiations from various directions are superimposed. Moreover, because irradiations from various directions are superimposed, it is difficult to correctly superimpose these irradiations; thus, unevenness in the beam irradiation amount may be caused. Still moreover, because a beam has a certain spread, an unnecessary beam may be irradiated onto a normal tissue in the vicinity of the place where irradiations are superimposed.

In contrast, in the scanning irradiation method, a diseased site is divided into small spots in the three dimensional space and respective necessary-amount beams are irradiated onto the small spots so that an irradiation field is formed in accordance with the shape of the whole diseased site; therefore, in principle, by selecting the spots, the scanning irradiation method can be applied to any diseased site shape; thus, the scanning irradiation method is an irradiation method having such a high degree of freedom that no collimator or bolus is required. Moreover, the amount of a beam to be irradiated can be adjusted for each spot; therefore, even in the case where irradiations from various directions are superimposed, the beam amount at the place where the irradiations are superimposed can be reduced. However, because a collimator or a bolus for preventing irradiation onto normal tissues other than the diseased site is not utilized, a high accuracy of the irradiation position is required. That is to say, there is required an irradiation-position accuracy that is higher than that required in a broad irradiation method.

Patent Document 1 discloses an invention in which in a particle beam therapy system utilizing a scanning irradiation method that requires a high accuracy in the beam irradiation position, an obstacle that causes beam dispersion is placed at a position that is as downstream in the beam as possible so that the beam size is reduced. The invention disclosed in Patent Document 1 is provided with a beam scanning apparatus that scans a charged particle beam, a first duct in which a beam extracting window is provided at a position that is at the downstream side of the beam scanning apparatus, an irradiation apparatus that makes a charged particle beam pass through the first duct and that irradiates the charged particle beam onto an irradiation subject, a second duct, and a beam transport apparatus that makes a charged particle beam, launched from an accelerator, pass through the second duct and that transports the charged particle beam to the irradiation apparatus; a beam position monitor (referred to simply as a position monitor, hereinafter) that measures the position of a charged particle beam is mounted in the beam extracting window through the intermediary of a holding member; a vacuum region in the first duct and a vacuum region in the second duct communicate with each other.

By use of a duct driving means and a duct extension/contraction means that extends and contracts the first duct in the beam-axis direction, the position monitor, which is provided at a position that is in the vicinity of and at the downstream side of the beam extracting window, is moved while the first duct moves in the beam-axis direction, so that the air gap between a patient and the beam extracting window is suppressed from becoming unnecessarily large and hence the beam size is reduced.

PRIOR ART REFERENCE

Patent Document

[Patent Document 1] Japanese Patent No. 4393581 (Paragraphs 0014, Paragraphs 0027 through 0029, FIG. 2)

DISCLOSURE OF THE INVENTION

Problems to be Solved by the Invention

In a scanning irradiation method, in order to obtain a high irradiation-position accuracy, it is required to accurately control the irradiation position and to accurately measure the irradiation position. That is because when the irradiation position cannot be measured, the therapy accuracy cannot be ensured and because when the irradiation position can be measured, the irradiation position can be fed back to irradiation control, i.e., the difference between the setting value and an actual irradiation position is corrected and then the irradiation is resumed.

In general, a dose required for the therapy is divided into a plurality of doses and then irradiation of a charged particle beam is performed; therefore, it is required that each time irradiation is performed, the position of the diseased site of a patient and the positions of a scanning electromagnet and a position monitor, which are apparatuses in a particle beam therapy system, are adjusted to match one another. In an ordinary particle beam therapy system, the positions of the scanning electromagnet and the position monitor are fixed. However, in the particle beam therapy system disclosed in Patent Document 1, the positions of the diseased site of a patient and the position monitor are moved each time irradiation is performed, i.e., the positions of the scanning electromagnet and the position monitor are moved; therefore, the positional relationship between the diseased site of the patient and the position monitor changes each time irradiation is performed, and the positional relationship between the scanning electromagnet and the position monitor also changes. In the case where as described above, the respective relative positions of the scanning electromagnet, the position monitor, and the patient diseased site change each time irradiation is performed, an extra calculation method is required in order to accurately calculate the irradiation position.

In the invention disclosed in Patent Document 1, in order to irradiate a small-size beam onto a patient diseased site, a position monitor is provided at the snout portion, which is the front end of the particle beam irradiation apparatus, and by use of a duct extension/contraction means and a duct driving means, the snout portion including the position monitor is made to approach the patient as much as possible so that the air gap between the patient and the beam extracting window is suppressed from becoming unnecessarily large. However, in the invention disclosed in Patent Document 1, no method for accurately calculating the beam irradiation position in a diseased site is disclosed. There has been a problem that when the positional relationship between the diseased site and the position monitor changes, i.e., in the case where even when the relative positions of the scanning electromagnet and the position monitor change, the beam irradiation position in the diseased site is not accurately calculated, irradiation cannot be performed with a high irradiation position accuracy.

The present invention has been implemented in order to solve the foregoing problems; the objective thereof is to obtain a particle beam irradiation apparatus in which by accurately calculating the beam irradiation position, high-accuracy beam irradiation can be performed even when the relative positions of the scanning electromagnet and the position monitor change.

Means for Solving the Problems

There are provided a scanning electromagnet that scans a charged particle beam in a direction that is perpendicular to a beam axis; a position monitor that is disposed in such a way that the relative position thereof to the scanning electromagnet in the beam axis direction can be changed to a desired position and that detects a passing position of the charged particle beam; and an irradiation control apparatus that calculates a position monitor distance information, which is a beam-axis distance from an irradiation plane on the irradiation subject to the position monitor, based on a beam-axis-direction position information on the position monitor, that is determined when irradiation onto the irradiation subject is performed, calculates a beam irradiation position on the irradiation subject, based on a detection signal from the position monitor and the calculated position monitor distance information, and then controls irradiation of the charged particle beam. The irradiation control apparatus includes a position calculation apparatus that calculates a beam irradiation position, on the irradiation plane, that is expressed based on a distance from an intersection point of the beam axis with the irradiation plane, based on a beam position detected by the position monitor, a scanning starting point distance information on a distance from the irradiation plane of the irradiation subject to a scanning starting point, of the charged particle beam, in the scanning electromagnet, and the position monitor distance.

Advantage of the Invention

In a particle beam irradiation apparatus according to the present invention, a beam irradiation position is calculated based on a beam position detected by a position monitor, the scanning starting point distance information, and the position monitor distance information; therefore, by accurately calculating the beam irradiation position, high-accuracy beam irradiation can be performed even when the relative position of a scanning electromagnet and the position monitor change.

BEST MODE FOR CARRYING OUT THE INVENTION

Embodiment 1

Figure 1:
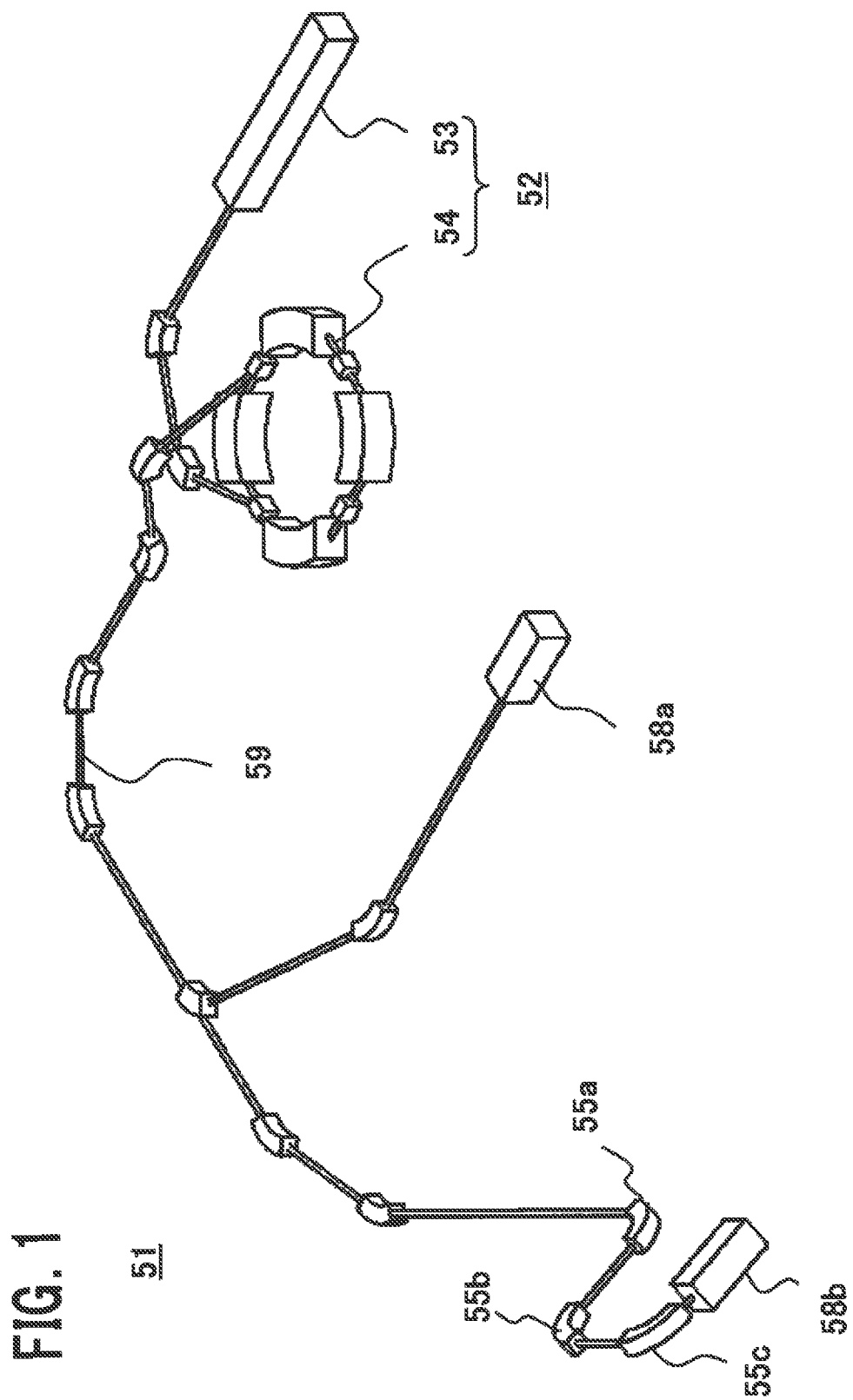
FIG. 1 is a schematic configuration diagram of a particle beam therapy system according to the present invention.

FIG. 1 is a schematic configuration diagram of a particle beam therapy system according to the present invention. A particle beam therapy system 51 includes a beam generation apparatus 52, a beam transport system 59, and particle beam irradiation apparatuses 58a and 58b. The beam generation apparatus 52 includes an ion source (unillustrated), a prestage accelerator 53, and a circular accelerator (simply referred to as an accelerator, hereinafter) 54, which is a synchrotron. The particle beam irradiation apparatus 58b is provided in a rotating gantry (unillustrated). The particle beam irradiation apparatus 58a is provided in a treatment room where no rotating gantry is installed. The function of the beam transport system 59 is to achieve communication between the accelerator 54 and the particle beam irradiation apparatuses 58a and 58b. A part of the beam transport system 59 is provided in the rotating gantry (unillustrated), and that part includes a plurality of deflection electromagnets 55a, 55b, and 55c.

A charged particle beam 2, which is a particle beam such as a proton beam generated in ion source or a carbon beam (heavy particle beam), is accelerated by the prestage accelerator 53 and enters the accelerator 54. The particle beam 2 is accelerated to obtain predetermined energy. The charged particle beam 2 is accelerated by the accelerator 54 in a high-frequency electric field up to 70% to 80% of the light velocity, as it is being bent by means of the magnets. The charged particle beam 2 launched from the accelerator 54 is transported to the particle beam irradiation apparatuses 58a and 58b by way of the beam transport system 59. The beam transport system 59 guides the charged particle beam 2, which has received sufficient energy, to the particle beam irradiation apparatuses 58a and 58b in respective designated treatment rooms through a path realized with a vacuum duct, while the orbit of the charged particle beam is changed by the electromagnets, as may be necessary. The particle beam irradiation apparatuses 58a and 58b each form an irradiation field in accordance with the size and the depth of the diseased site of a patient 24 as an irradiation subject 25 (refer to FIG. 2), and each irradiate the charged particle beam 2 onto the irradiation subject 25.

Figure 2:
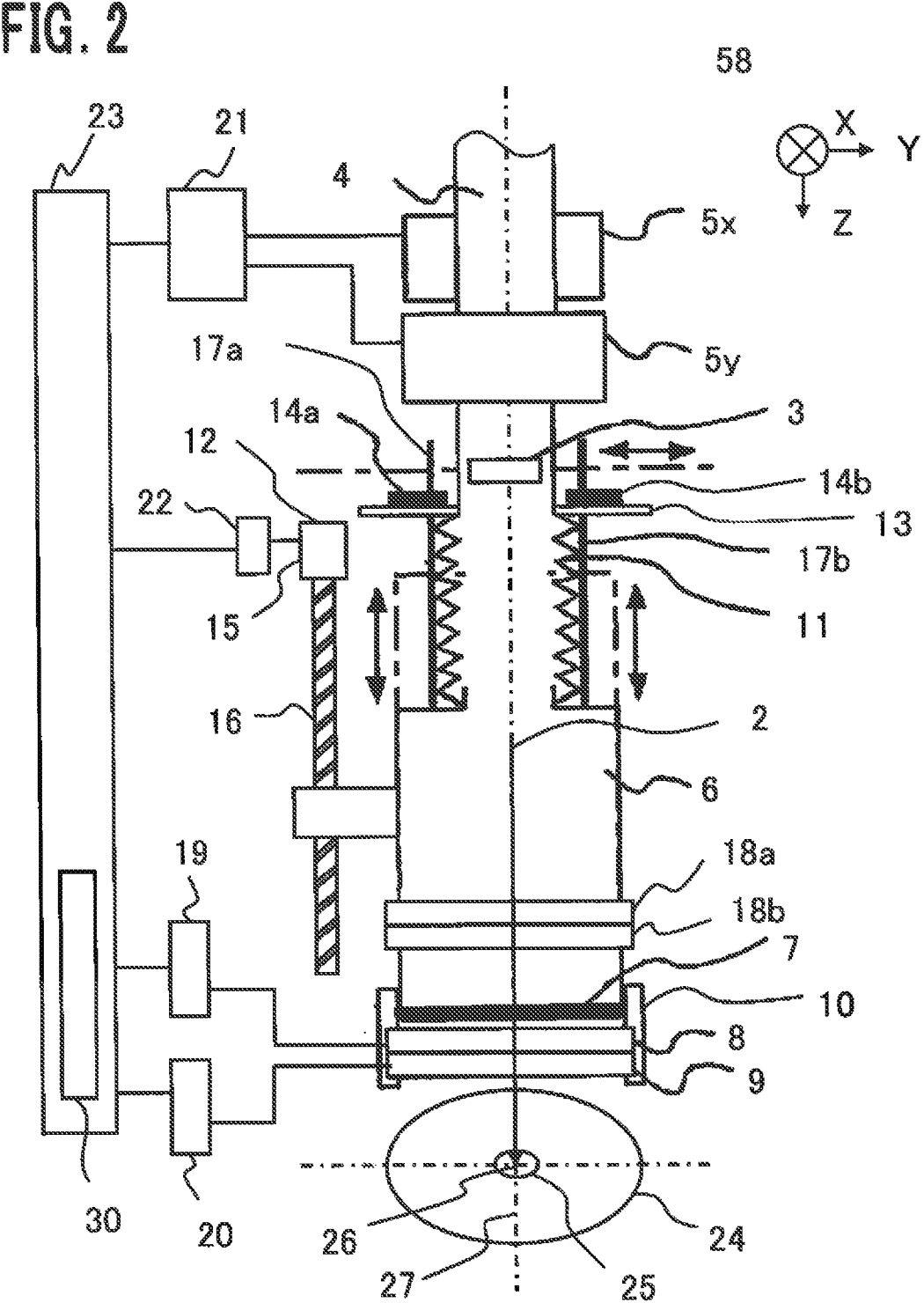
FIG. 2 is a configuration diagram illustrating a particle beam irradiation apparatus according to Embodiment 1 of the present invention.

FIG. 2 is a configuration diagram illustrating a particle beam irradiation apparatus according to Embodiment 1 of the present invention. A charged particle beam 2 generated in the beam generation apparatus 52 and accelerated to gain predetermined energy is led to the particle beam irradiation apparatus 58 by way of the beam transport system 59. The particle beam irradiation apparatus 58 is provided with vacuum ducts 4 and 6 that ensure a vacuum region from the beam transport system 59 and communicate with each other; X-direction and Y-direction scanning electromagnets 5x and 5y that scan the charged particle beam 2 in the X direction and the Y direction, respectively, which are directions perpendicular to the charged particle beam 2; a position monitor 3 situated at the upstream side; a beam extracting window 7 that extracts the charged particle beam 2; a dose monitor 8; a position monitor 9 situated at the downstream side; a scanning electromagnet power source 21; a duct driving device 12 that moves the vacuum duct 6 toward the beam axis; a duct extension/contraction device 11 that extends and contracts the vacuum ducts 4 and 6; a distance sensor 22 that detects the Z-direction position (the distance from a reference point) of the position monitor 9; a dose data converter 19; a position data converter 20; and an irradiation control apparatus 23 that controls the irradiation-system apparatuses of the particle beam irradiation apparatus 58. The charged particle beam 2 is irradiated along a center axis 27 indicated in FIG. 2; adjustment is performed in such a way that the charged particle beam 2 eventually heads for an isocenter (irradiation reference point) 26 unless the X-direction scanning electromagnet 5x and the Y-direction scanning electromagnet 5y perform any control of the charged particle beam 2. The traveling direction of the charged particle beam 2 is the Z direction.

The X-direction and Y-direction scanning electromagnets 5x and 5y scan the charged particle beam 2 in the X direction and the Y direction, respectively. The position monitors 3 and 9 each detect the gravity center of a beam and a beam peak position (passing position) through which the charged particle beam 2 that has been scanned by the X-direction scanning electromagnet 5x and the Y-direction scanning electromagnet 5y passes. The dose monitor 8 detects the dose of the charged particle beam 2. The scanning electromagnet power source 21 changes setting currents for the X-direction scanning electromagnet 5x and the Y-direction scanning electromagnet 5y, based on control inputs (command currents), which are outputted from the irradiation control apparatus 23 to the X-direction scanning electromagnet 5x and the Y-direction scanning electromagnet 5y.

The irradiation control apparatus 23 controls the irradiation position of the charged particle beam 2 on the irradiation subject 25, based on treatment plan data generated by an unillustrated treatment planning apparatus; when the dose measured by the dose monitor 8 and converted into digital data by the dose data converter 19 reaches the desired dose, the charged particle beam 2 is stopped. In other words, the irradiation control apparatus 23 controls the irradiation spot and the irradiation dose at the irradiation subject 25. The irradiation spots are layers divided in the Z direction; each irradiation spot is divided into a slice, which corresponds to the kinetic energy of the charged particle beam 2, and the XY-direction small regions in the slice. The irradiation control apparatus 23 scans the charged particle beam 2 onto respective slices, of the irradiation subject 25, that are layers corresponding to kinetic energy levels.

The duct driving device 12 includes a motor 15 and a ball screw 16; the ball screw 16, rotated by the motor 15, moves the vacuum duct 6 through the intermediary of a female screw mechanism fixed to the vacuum duct 6. The duct extension/contraction device 11 connects the vacuum duct 4 with the vacuum duct 6; the duct extension/contraction device 11 extends and contracts the vacuum duct 4 and the vacuum duct 6. The duct extension/contraction device 11 is, for example, a bellows. Reference characters 17a and 17b are guide rods, one end of each of which is fixed to the vacuum duct 6 and the other end penetrates a supporting plate 13 fixed to the vacuum duct 4. The guide rods 17a and 17b are supported by bearings 14a and 14b, respectively. When the duct driving device 12 moves the vacuum duct 6, the bearings 14a and 14b smoothly move the duct extension/contraction device 11 in the Z direction, and hence the vacuum duct 6 smoothly moves. The dose monitor 8 and the position monitor 9 are held at the front end of the vacuum duct 6 by a holding member 10. The vacuum duct 6 is an example in which two ducts are connected with each other by use of flanges 18a and 18b. The duct driving device 12 is a driving device for changing the relative positions of the scanning electromagnets 5x and 5y and the position monitor 9 in the beam axis direction (the direction of the center axis 27).

Figure 3:
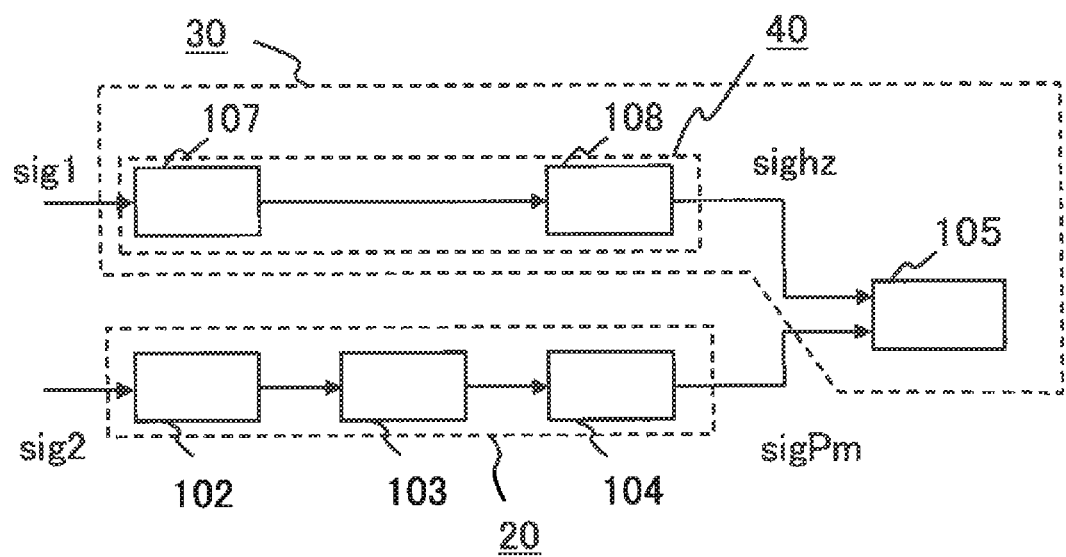
FIG. 3 is a block diagram illustrating the configuration of a position calculation apparatus in FIG. 2.

The irradiation control apparatus 23 includes a position calculation apparatus 30 for calculating the irradiation position of the charged particle beam 2 on the irradiation subject 25. FIG. 3 is a block diagram illustrating the configuration of the position calculation apparatus 30 according to Embodiment 1. The position calculation apparatus 30 includes a current/voltage converter (I/V converter) 107, an analogue/digital converter (A/D converter) 108, and a signal processing device 105. The distance sensor 22 illustrated in FIG. 2 is an encoder that detects the rotation of the motor 15 in the duct driving device 12. A current signal sig1 from the distance sensor 22 passes through the I/V converter 107 so as to be converted into a voltage, and is converted from an analogue signal into a digital signal by the A/D converter 108. A digital signal sighz is inputted to the signal processing device 105.

The position monitor 3 (9) is formed, for example, of a multiple-wire proportional counter tube in which a group of vertical wires are stretched in a gas that ionizes a particle beam. A current signal sig2, which is a beam position information on the position monitor 9, passes through the I/V converter 102 so as to be converted into a voltage; then, the current signal sig2 is amplified by an amplifier 103 and is converted from an analogue signal into a digital signal by the A/D converter 104. A digital signal sigPm is inputted to the signal processing device 105. The I/V converter 102, the amplifier 103, and the A/D converter 104 configure the position data converter 20. A current signal detected by the position monitor 3 is converted into a digital signal by another unillustrated position data converter.

The signal processing device 105 derives a beam position Pm (Xpm, Ypm) on the position monitor from calculation of, for example, the gravity center of the charged particle beam 2, a beam peak position, and the like. A Z-axis-direction information on the position monitor 9, for example, the distance hz1 from the X-direction scanning electromagnet 5x and the distance hz2 (refer to FIG. 5A and FIG. 5B) from the Y-direction scanning electromagnet 5y are calculated based on a signal detected by the distance sensor 22. The signal processing device 105 calculates the beam irradiation position P (Xp, Yp, Zp), based on the Z-direction information on the position monitor 9, the beam position Pm (Xpm, Ypm), the distance D from the after-mentioned reference point (e.g., a skin surface 34) to the position monitor 9b, the energy of the charged particle beam 2, so that the beam position Pm is converted into the beam irradiation position P (Xp, Yp, Zp).

Figure 4:
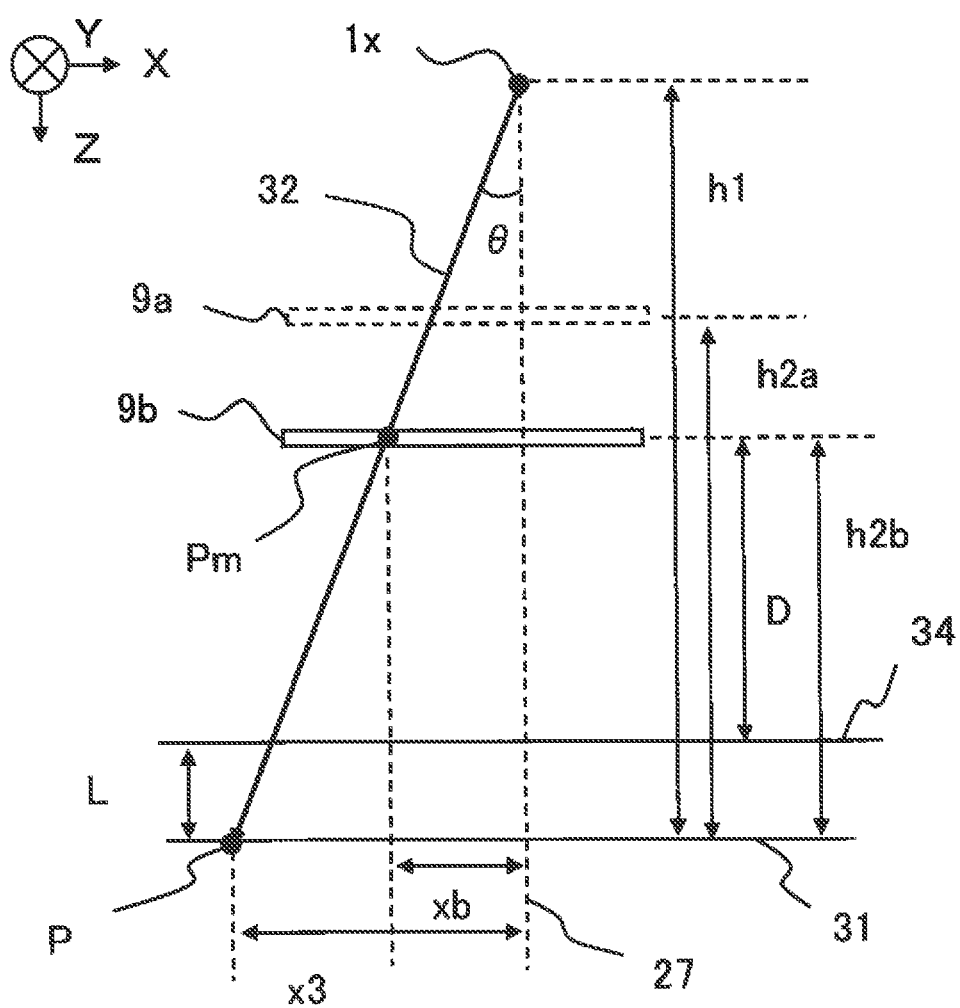
FIG. 4 is a diagram for explaining a position calculation method according to Embodiment 1 of the present invention.
Figure 5A:
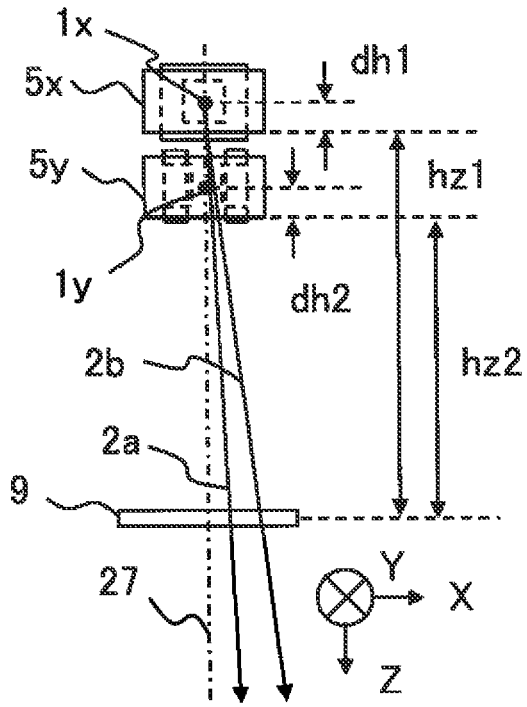
FIG. 5A and FIG. 5B are diagrams illustrating the scanning starting point in FIG. 4.
Figure 5B:
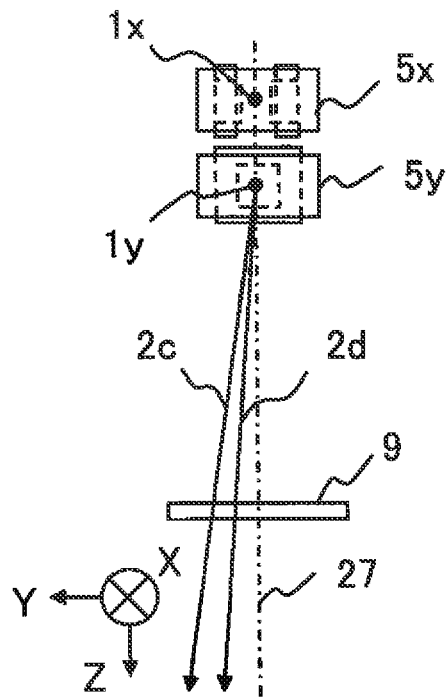

Next, the method of calculating the beam irradiation position P (Xp, Yp, Zp) for the diseased site of the patient 24 will be explained. FIG. 4 is a diagram for explaining a position calculation method according to Embodiment 1 of the present invention; FIG. 5A and FIG. 5B are diagrams representing scanning starting points. As described above, the charged particle beam 2 is scanned by the X-direction scanning electromagnet 5x and the Y-direction scanning electromagnet 5y. While passing through the scanning electromagnet 5x (5y), the charged particle beam 2 is gradually deflected by a magnetic field generated by the scanning electromagnet 5x (5y). The launching direction at a time when the charged particle beam 2 exits from the scanning electromagnet 5x (5y) is different from the incident direction at a time when the charged particle beam enters the scanning electromagnet 5x (5y). In order to calculate the beam irradiation position P (Xp, Yp, Zp) for the diseased site of the patient 24, it is assumed that the charged particle beam 2 is scanned in such a way as to change its direction at a single point in the scanning electromagnet 5x (5Y). The single point at which the charged particle beam 2 changes its direction in the X-direction scanning electromagnet 5x will be referred to as a scanning starting point 1x. Similarly, the single point at which the charged particle beam 2 changes its direction in the Y-direction scanning electromagnet 5y will be referred to as a scanning starting point 1y. For example, the scanning starting point 1x is defined to be the Z-direction center point of the X-direction scanning electromagnet 5x. Similarly, the scanning starting point 1y is defined to be the Z-direction center point of the Y-direction scanning electromagnet 5y.

The particle beam irradiation apparatus 58 illustrated in FIG. 2 is an example where the X-direction scanning electromagnet 5x is disposed at the upstream side and the Y-direction scanning electromagnet 5y is disposed at the downstream side of the X-direction scanning electromagnet 5x. As illustrated in FIG. 5A and FIG. 5B, the scanning starting point 1x is situated at the upstream side of the scanning starting point 1y. FIG. 5A is a schematic diagram at a time when the scanning electromagnets 5x and 5y are viewed along the Y direction. FIG. 5B is a schematic diagram at a time when the scanning electromagnets 5x and 5y are viewed along the X direction. At the scanning starting point 1x, the charged particle beam 2 is scanned in the X direction, as the charged particle beams 2a or 2b. At the scanning starting point 1y, the charged particle beam 2 is scanned in the Y direction, as the charged particle beams 2c or 2d.

With reference to FIG. 4, a position calculation method according to Embodiment 1 will be explained in detail. FIG. 4 illustrates an example where the charged particle beam 2 is scanned by the X-direction scanning electromagnet 5x. The charged particle beam 2 scanned at the scanning starting point 1x passes through the position monitor 9b, as indicated by a trajectory 32, and then is irradiated onto the diseased site (irradiation subject 25) of the patient 24. Reference numeral 34 denotes a skin surface of the patient 24; reference numeral 31 denotes an irradiation plane that passes through a given slice. The length L from the skin surface 34 to the irradiation plane 31 corresponds to a range L of the charged particle beam 2, up to which the charged particle beam 2 enters the patient 24 in accordance with the energy thereof. The range L corresponds to the length from the skin surface 34 to the Bragg peak BP of the charged particle beam 2. The distance D from the skin surface 34 to the position monitor 9b is measured when a patient positioning work is performed. For example, the position of a diseased site and the position monitor 9b are observed, and then the distance D is measured based on the images by an X-ray image-capturing device. The positioning work signifies work in which while the position of a diseased site is being monitored by the X-ray image-capturing device, the posture adjustment (angle adjustment) of a treatment table, on which the patient 24 is fixed, is implemented in such a way that a particle beam is irradiated onto the diseased site along a direction determined at the stage of making a treatment plan and in which the position and the posture of the diseased site are made to coincide with the planned value with respect to the isocenter, which is the irradiation center.

In this situation, it is assumed that the position of the position monitor 9 has changed from the position of the position monitor 9a, which is illustrated by a broken line, to the position of the position monitor 9b, which is illustrated by a solid line. At this moment, the distance (position monitor distance information) from the irradiation plane 31 of the diseased site to the position monitor 9 changes from h2a to h2b. The charged particle beam 2 passes through the beam position Pm, which is a measurement point on the position monitor 9b, and reaches the beam irradiation position P on the irradiation plane of the diseased site. Because the position coordinates in the X direction is calculated, the points in FIG. 4, i.e., the scanning starting point 1x, the beam position Pm, and the beam irradiation position P will be expressed with X and Z coordinates, while the Y coordinate is omitted. The scanning starting point 1x is considered as the origin coordinates (0, 0) of the XZ coordinate system. In the XZ coordinate system, the beam position Pm and the beam irradiation position P are expressed as (Xpm, Zpm) and (Xp, Zp), respectively. The X-direction length from the center axis 27, which passes through the scanning starting point 1x (0, 0), to the beam position Pm (Xpm, Zpm) is expressed as "xb", and the X-direction length from the center axis 27 to the beam irradiation position P (Xp, Zp) is expressed as "x3". Letting θ and h1 denote the angle (after-mentioned scanning angle) between the center axis 27 and the trajectory 32 and the distance (scanning starting point distance information) from the scanning starting point 1x to the irradiation plane 31, respectively, the lengths x3 and xb can be expressed by the equation (1) and the equation (2), respectively.

$$x3 = h1 \cdot \tan\theta \tag{1}$$

$$xb = (h1 - h2b) \cdot \tan\theta \tag{2}$$

By substituting tan θ, obtained from the equation (1), for tan θ in the equation (2), the equation (3) is obtained.

$$x3 = h1 \cdot xb/(h1 - h2b) \tag{3}$$

The Y-direction length from the center axis 27 to the beam irradiation position P can also be calculated by an equation similar to the equation (3).

Figure 6:
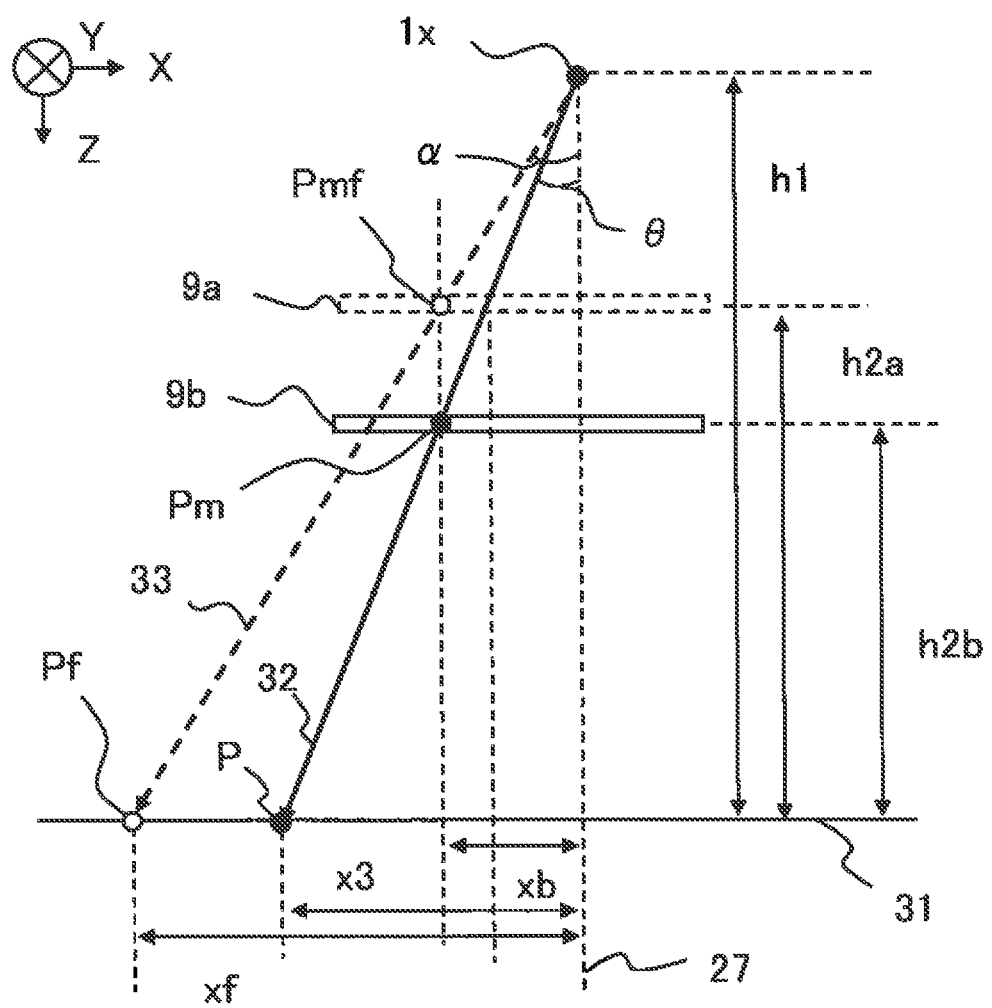
FIG. 6 is a diagram for explaining the advantage of a position calculation method according to Embodiment 1 of the present invention.

In the case where although as described above, the distance from the irradiation plane 31 of the diseased site to the position monitor 9 has changed from h2a to h2b, the distance information for the position monitor 9 at the time when the charged particle beam 2 is irradiated cannot be utilized, the beam irradiation position is calculated by use of the initial-state distance of the position monitor 9, i.e., the distance h2a of the position monitor 9a. With reference to FIG. 6, the advantage of the position calculation method according to Embodiment 1 of the present invention will be explained. The beam irradiation position is calculated in the same manner as described above under the assumption that the distance between the irradiation plane 31 and the position monitor 9 is h2a, which is the distance of the position monitor 9a. In this case, there is caused false recognition that the trajectory 32 of the charged particle beam 2 is a virtual trajectory 33. It is assumed that Pmf (Xpmf, Zpmf) and Pf (Xpf, Zpf) denote the virtual beam position of the position monitor 9a and the virtual calculation beam irradiation position, respectively. Letting a denote the angle between the center axis 27 and the virtual trajectory 33, the X-direction length xf from the center axis 27 to the virtual beam irradiation position Pf can be expressed by the equation (4) in the same manner as the method utilized to obtain the equation (3).

$$xf = h1 \cdot xb/(h1 - h2a) \tag{4}$$

Here, the advantage of the position calculation method according to Embodiment 1 will be examined based on the ratio of x3 to xf. Through calculation by use of the equations (3) and (4), x3/xf (the ratio of x3 to xf) is expressed by the equation (5).

$$x3/xf = (h1 - h2a)/(h1 - h2b) \tag{5}$$

In a typical particle beam therapy system, the distances h1 and h2a are 3000 mm and 600 mm, respectively. In the case where the distance h2b is 300 mm, i.e., in the case where through the duct driving device 12, the vacuum duct 6 is headed for the patient 24 by 300 mm, calculation through the equation (5) results in "0.89". The position calculation method according to Embodiment 1 can reflect on the result the information that the relative positions of the scanning electromagnet and the position monitor have changed; therefore, the accuracy of calculation of the beam irradiation position P for the diseased site of the patient 24 can be improved by more than 10%, in comparison with a method in which the information that the relative positions of the scanning electromagnet and the position monitor have changed cannot be reflected on the result.

The position calculation method according to Embodiment 1 can reflect on the result the information that the relative positions of the scanning electromagnet and the position monitor have changed; therefore, the beam irradiation position can accurately be calculated. Accordingly, in the particle beam irradiation apparatus and the particle beam therapy system to which this position calculation method is applied, the charged particle beam 2 can accurately be irradiated onto the diseased site of the patient 24 as the irradiation subject 25. Thus, it is made possible to treat a diseased site, such as a brain tumor or the like, that requires a high accuracy of the irradiation position.

It has already been described that in a scanning irradiation method, there is required an irradiation-position accuracy that is higher than that required in a broad irradiation method. Here, the reason why a high accuracy of the beam irradiation position is required will be described in detail. In a broad irradiation method in which a charged particle beam is flatly spread in the three dimensions, even when the irradiation position is slightly displaced, the portion of the beam other than the fringe of the beam that has spread in the three-dimensional space can appropriately be irradiated. However, in the scanning irradiation method, when the irradiation position is displaced, not only a beam cannot be irradiated onto a desired spot, but also the beam is erroneously irradiated onto a spot other than the desired spot. In the case where a beam cannot be irradiated onto a cancer cell situated at the desired spot, the effect of the therapy is reduced. Moreover, in some cases, a beam is erroneously irradiated onto a spot that is a major organ onto which any particle beam should not be irradiated. Erroneous irradiation in a scanning irradiation method poses a larger problem than a broad irradiation method because the amount of particle beams to be irradiated per time and per irradiation volume in the scanning irradiation method is larger than that in the broad irradiation method. Furthermore, when the irradiation position is displaced, the advantage, of a scanning irradiation method, that the amount of beams to be irradiated is adjusted for each spot cannot effectively be utilized. Again, for that reason, a high accuracy of the irradiation position is required.

The signal processing device 105 in the position calculation apparatus 30 is provided with a CPU and a memory and implements the foregoing position calculation method through software. Based on the signal sighz obtained through converting the current signal sig1 from the distance sensor 22 into a digital signal, the signal processing device 105 calculates the distance hz1 from a reference (e.g., the bottom portion of the electromagnet iron core illustrated in FIG. 5A and FIG. 5B) in the X-direction scanning electromagnet 5x to the position monitor 9 and the distance hz2 from a reference (e.g., the bottom portion of the electromagnet iron core illustrated in FIG. 5A and FIG. 5B) in the Y-direction scanning electromagnet 5y to the position monitor 9. The signal processing device 105 performs the following calculation by use of a distance dh1 from the reference in the X-direction scanning electromagnet 5x, which is stored in the memory, to the scanning starting point 1x and a distance dh2 from the reference in the Y-direction scanning electromagnet 5y, which is stored in the memory, to the scanning starting point 1y.

The signal processing device 105 calculates the range L, based on an energy information on the charged particle beam 2 to be irradiated and a slice information on the irradiation subject 25. Based on the distance hz1, the distance dh1, the range L, and the distance D from the position monitor 9 to the skin surface 34, the signal processing device 105 calculates, through the equations (6) and (7), the distance h1 from the scanning starting point 1x to the irradiation plane 31 and the distance h2b from the position monitor 9 to the irradiation plane 31. Based on the distance hz2, the distance dh2, the range L, and the distance D, the signal processing device 105 calculates also a distance h1y from the scanning starting point 1y to the irradiation plane 31, through the equation (8). Here, it is assumed that the scanning starting point 1y is on the center axis 27, without considering the effect of the X-direction scanning electromagnet 5x.

$$h1 = hz1 + dh1 + D + L \tag{6}$$

$$h2b = D + L \tag{7}$$

$$h1y = hz2 + dh2 + D + L \tag{8}$$

The signal processing device 105 calculates the beam position Pm (Xpm, Ypm), based on the signal sigPm (sigPmx, sigPmy) obtained by converting the current signal sig2 (sig2x, sig2y) from the position monitor 9 into a digital signal. The length from the center axis 27 to the beam position Pm is calculated, so that xb and yb are obtained. The length xb, illustrated in FIG. 4, is an X-direction length from the center axis 27 to the beam position Pm. The length yb is an Y-direction length from the center axis 27 to the beam position Pm. The signal processing device 105 calculates the X-direction length x3 from the center axis 27 to the beam irradiation position P, through the equation (3). Similarly, the Y-direction length y3 is calculated through the equation (9).

$$y3 = h1y \cdot yb/(h1y - h2b) \tag{9}$$

A moving device, unillustrated in FIG. 2, can set the position monitor 3 at a place through which the charged particle beam 2 does not pass. In the particle beam irradiation apparatus 58 according to Embodiment 1, when the charged particle beam 2 is irradiated, the beam position Pm (Xpm, Ypm), which is a passing position of the charged particle beam 2, is measured only by the position monitor 9; therefore, the obstacle that causes scatter of the charged particle beam 2 can be diminished as much as possible, and the beam extracting window 7, the dose monitor 8, and the position monitor 9, which become the obstacles that cause the scatter of the charged particle beam 2, can be arranged at the downstream side. Thus, the beam size of the charged particle beam 2 can be reduced. Moreover, when the position calculation method according to Embodiment 1 is utilized, the charged particle beam 2 of a small beam size can accurately be irradiated onto the diseased site of the patient 24 as the irradiation subject 25.

There exists another advantage in the capability of accurately calculating a beam irradiation position. For example, even in the case where after the position of an irradiation spot in given order is calculated through the foregoing calculation method, it is recognized that the calculated spot position is displaced from the desired irradiation position in a treatment plan, it is made possible that when the dose value of the irradiation spot at the calculated position is read and then reaches the dose value for that position, the beam is scanned on the originally planned irradiation spot. In this situation, the irradiation control apparatus 23 calculates the difference between the predetermined irradiation position and the actual irradiation position, corrects control inputs (command currents) for the X-direction scanning electromagnet 5x and the Y-direction scanning electromagnet 5y, and then sends the corrected control inputs to the scanning electromagnet power source 21, so that in a slice where the energy of the charged particle beam 2 is the same, the charged particle beam 2 of the planned desired dose can be scanned on the planned desired position. Through the foregoing method, the desired dose of a spot at a displaced place is managed, so that irradiation onto the diseased site can be continued without interrupting the irradiation of the charged particle beam 2.

As described above, the particle beam irradiation apparatus according to Embodiment 1 is provided with the scanning electromagnets 5x and 5y that each scan the charged particle beam 2 in the respective directions perpendicular to the beam axis 27; the position monitor 9 that is disposed in such a way that the relative position thereof to the scanning electromagnets 5x and 5y in the beam axis direction can be changed to a desired position and that detects a passing position of the charged particle beam 2; and the irradiation control apparatus 23 that calculates the beam-axis distance D from a predetermined reference point to the position monitor 9, based on the beam-axis-direction position information on the position monitor 9, calculates the beam irradiation position on the irradiation subject 25, based on a detection signal from the position monitor 9 and the calculated distance D, and then controls the irradiation of the charged particle beam 2. In addition, the irradiation control apparatus 23 includes the position calculation apparatus 30 that calculates the beam irradiation position P on the irradiation plane 31 of the irradiation subject 25, based on the beam position Pm detected by the position monitor 9, the scanning starting point distance information on a distance from the irradiation plane 31 of the irradiation subject 25 to the scanning starting point 1x or 1y, of the charged particle beam 2, in the scanning electromagnet 5x or 5y, and the position monitor distance information on a distance from the irradiation plane 31 to the position monitor 9, that is calculated based on the calculated distance D. As a result, by accurately calculating the beam irradiation position P, high-accuracy beam irradiation can be performed even when the relative position of the scanning electromagnet 5x or 5y to the position monitor 9 changes.

The particle beam therapy system 51 according to Embodiment 1 is provided with the beam generation apparatus 52 that generates the charged particle beam 2 and accelerates it by means of the accelerator 54; the beam transport system 59 that transports the charged particle beam 2 accelerated by the accelerator 54; and the particle beam irradiation apparatus 58 that irradiates the charged particle beam 2 transported by the beam transport system 59 onto the irradiation subject 25. The particle beam irradiation apparatus 58 is provided with the scanning electromagnets 5x and 5y that each scan the charged particle beam 2 in the respective directions perpendicular to the beam axis 27; the position monitor 9 that is disposed in such a way that the relative position thereof to the scanning electromagnets 5x and 5y in the beam axis direction can be changed to a desired position and that detects a passing position of the charged particle beam 2; and the irradiation control apparatus 23 that calculates the beam-axis distance D from a predetermined reference point to the position monitor 9, based on the beam-axis-direction position information on the position monitor 9, calculates the beam irradiation position on the irradiation subject 25, based on a detection signal from the position monitor 9 and the calculated distance D, and then controls the irradiation of the charged particle beam 2. The irradiation control apparatus 23 includes the position calculation apparatus 30 that calculates the beam irradiation position P on the irradiation plane 31 of the irradiation subject 25, based on the beam position Pm detected by the position monitor 9, the scanning starting point distance information on a distance from the irradiation plane 31 of the irradiation subject 25 to the scanning starting point 1x or 1y, of the charged particle beam 2, in the scanning electromagnet 5x or 5y, and the position monitor distance information on a distance from the irradiation plane 31 to the position monitor 9, that is calculated based on the calculated distance D. As a result, by accurately calculating the beam irradiation position P, high-accuracy beam irradiation can be performed even when the relative position of the scanning electromagnet 5x or 5y to the position monitor 9 changes.

Embodiment 2

In Embodiment 1, there has been described the method in which the beam irradiation position P (Xp, Yp, Zp) for the diseased site of the patient 24 is calculated by use of only the measurement result in the position monitor 9; however, when the information on the scanning angle (deflection angle) θ is obtained from the measurement result in the position monitor 3 and the measurement result in the position monitor 9, it is made possible to correct the result of the position calculation; thus, the accuracy of calculating the beam irradiation position on the diseased site of the patient 24 can further be raised. The scanning angle θ is the angle between the trajectory 32 of the charged particle beam 2 scanned by the scanning electromagnets 5x (5y) and the beam axis (center axis 27).

Figure 7:
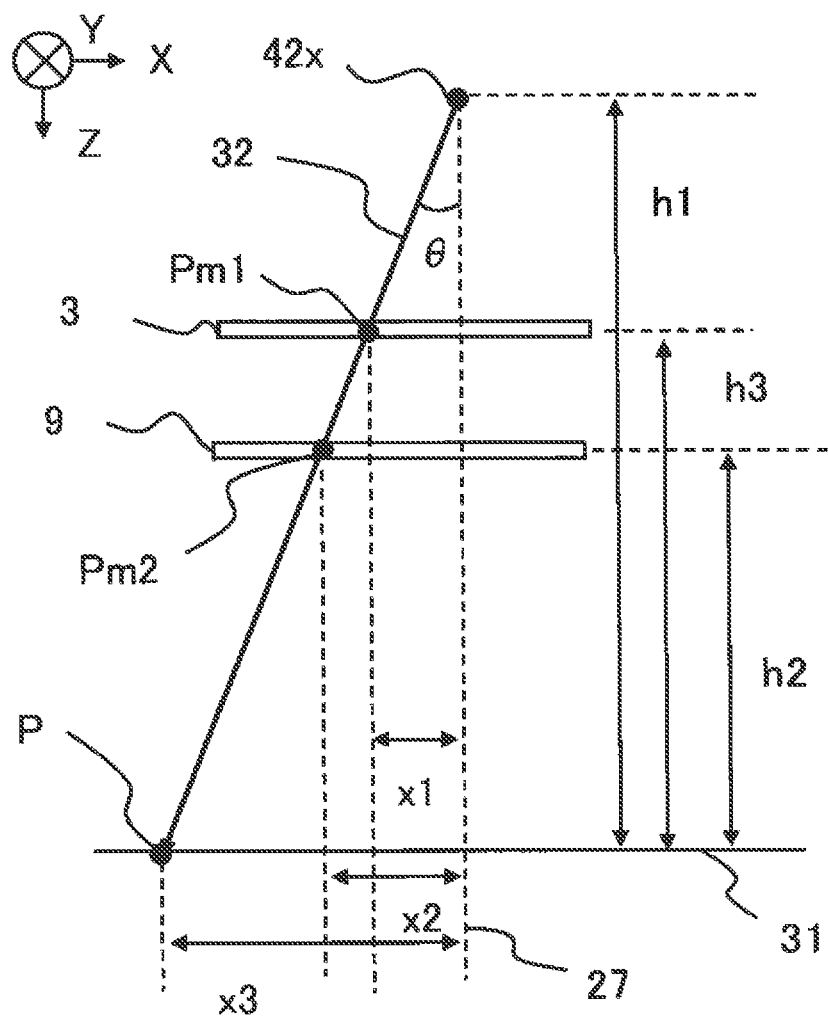
FIG. 7 is a diagram for explaining a position calculation method according to Embodiment 2 of the present invention.

FIG. 7 is a diagram for explaining a position calculation method according to Embodiment 2 of the present invention. FIG. 7 illustrates an example where the charged particle beam 2 is scanned by the X-direction scanning electromagnet 5x. The charged particle beam 2 is scanned at a scanning starting point 42x, passes through a beam position Pm1 on the position monitor 3 and a beam position Pm2 on the position monitor 9, and reaches the beam irradiation position P on the irradiation plane 31 of the diseased site. In comparison with FIG. 4 with which the position calculation method according to Embodiment 1 has been explained, a distance h3 from the irradiation plane 31 of the diseased site to the position monitor 3 and an X-direction length x1 from the center axis 27 that passes through the scanning starting point 1x (0, 0) to the beam position Pm1 (Xpm1, Ypm1) are added. Reference character x2 denotes the X-direction length from the center axis 27 to the beam position Pm2 (Xpm2, Ypm2). A tan θ can be given by the equation (10).

$$\tan\theta = (x2-x1)/(h3-h2) \quad (10)$$

The X-direction length x3 from the center axis 27 to the beam irradiation position P (Xp, Zp) can be given by the equation (11). By substituting the equation (10) for the equation (11), the equation (12) is obtained.

$$x3 = x1 + h3\cdot\tan\theta \quad (11)$$

$$x3 = x1 + h3\cdot(x2-x1)/(h3-h2) \quad (12)$$

Because being the same as h2b in the equation (7), h2 can be calculated based on the range L and the distance D from the position monitor 9 to the skin surface 34. The position of the position monitor 3 does not change in the particle beam irradiation apparatus 58 even when the vacuum duct 6 (position monitor 9) moves. By use of the Z-axis-direction information on the position monitor 3, which is an information inherent to the apparatus, for example, a distance hz3 from the X-direction scanning electromagnet 5x to the position monitor 3 or a distance hz4 from the Y-direction scanning electromagnet 5y to the position monitor 3, the distance h3 is calculated through the equation (13) or (14).

$$h3 = (hz1-hz3) + D + L \quad (13)$$

$$h3 = (hz2-hz4) + D + L \quad (14)$$

As is the case with Embodiment 1, based on the signal sighz obtained through converting the current signal sig1 from the distance sensor 22 into a digital signal, the signal processing device 105 in the position calculation apparatus 30 calculates the distance hz1 from a reference in the X-direction scanning electromagnet 5x to the position monitor 9 and the distance hz2 from a reference in the Y-direction scanning electromagnet 5y to the position monitor 9. The signal processing device 105 calculates the distances h2 and h3 through the equations (7) and (13) or the equations (7) and (14).

The signal processing device 105 calculates the beam position Pm2 (Xpm2, Ypm2), based on the signal sigPm (sigPmx, sigPmy) obtained by converting the current signal sig2 (sig2x, sig2y) from the position monitor 9 into a digital signal. Similarly, the signal processing device 105 calculates the beam position Pm1 (Xpm1, Ypm1), based on a signal sigPm3 (sigPm3x, sigPm3y) obtained by converting a current signal sig3 (sig3x, sig3y) from the position monitor 3 into a digital signal. The signal processing device 105 calculates the length from the center axis 27 to the beam position Pm1, so that x1 and y1 are obtained. The signal processing device 105 calculates the length from the center axis 27 to the beam position Pm2, so that x2 and y2 are obtained. Characters y1 and y2 denote the Y-direction length from the center axis 27 to the beam position Pm1 and the Y-direction length from the center axis 27 to the beam position Pm2, respectively.

In the position calculation method according to Embodiment 2, the information on the scanning angle θ can be obtained, and the beam irradiation position P (Xp, Yp, Zp) for the diseased site of the patient 24 is calculated by use of the scanning angle θ; therefore, the position calculation method according to Embodiment 2 makes it possible to calculate the beam irradiation position P in a more accurate manner than the position calculation method according to Embodiment 1. In Embodiment 1, the calculation is implemented under the assumption that the scanning starting point 1x of the X-direction scanning electromagnet 5x and the scanning starting point 1y of the Y-direction scanning electromagnet 5y are always fixed. Accordingly, as the scanning angle θ, there is utilized the angle between a line that connects the beam position Pm2 (Xpm2, Ypm2) with the scanning starting point 1x or 1y and the center axis 27 that passes through the scanning starting points 1x and 1y. In contrast, in Embodiment 2, the scanning angle θ can accurately be obtained by use of the two position monitors 3 and 9. Therefore, even if the scanning starting point 42x or a scanning starting point 42y (the scanning starting point of the Y-direction scanning electromagnet 5y) illustrated in FIG. 7 is different from the assumed point, the beam irradiation point P (Xp, Yp, Zp) for the diseased site of the patient 24 can accurately be calculated. In the position calculation method according to Embodiment 2, the beam irradiation position P (Xp, Yp, Zp) for the diseased site of the patient 24 can be calculated in a more accurate manner than in the position calculation method according to Embodiment 1; therefore, the particle beam irradiation apparatus 58 and the particle beam therapy system 51 utilizing the position calculation method according to Embodiment 2 make it possible to perform beam irradiation in a more accurate manner than those utilizing the position calculation method according to Embodiment 1.

The position calculation method according to Embodiment 2 can also be applied to a case, described in after-mentioned Embodiment 3, in which the scanning starting point changes depending on the scanning angle, a case, described in after-mentioned Embodiment 4, in which the scanning starting point changes depending on the angle at which the charged particle beam 2 enters the scanning electromagnet 5x or 5y, and a case in which due to another reason, the scanning starting point changes.

Embodiment 3

In Embodiment 1, there has been described a case where the calculation is implemented under the assumption that the scanning starting point 1x of the X-direction scanning electromagnet 5x and the scanning starting point 1y of the Y-direction scanning electromagnet 5y are always fixed; however, strictly speaking, the scanning starting point changes depending on the scanning angle at the scanning starting point. In Embodiment 3, the beam irradiation position P (Xp, Yp, Zp) for the diseased site of the patient 24 is calculated based on the position of the scanning starting point at each scanning angle and data on the trajectory of a scanned beam. As a result, the calculation accuracy can further be raised.

In a position calculation method according to Embodiment 3, the beam irradiation position P (Xp, Yp, Zp) for the diseased site of the patient 24 is calculated by use of only the position monitor 9 when the charged particle beam 2 is irradiated in the therapy. Accordingly, by use of the two position monitors 3 and 9 and through an experiment, the position of the scanning starting point at each scanning angle and data on the trajectory of a scanned beam is obtained, and then the characteristic, represented in FIG. 8, between the scanning angle θ and the distance dh from the reference in the scanning electromagnet 5 (only "5" is utilized without distinguishing 5x and 5y from each other, as may be necessary) to the scanning starting point 1 (1x, 1y) is obtained.

With reference to FIG. 7, a case where the charged particle beam 2 is irradiated at a given scanning angle θ will be explained. By utilizing the two position monitors 3 and 9, the scanning angle θ can be calculated through the equation (10). Because h1 is x3/tan θ, this h1 is substituted for h1 in the equation (6) and then the equation (6) is modified, so that dh1 can be given by the equation (15).

$$dh1 = x3/\tan\theta - D - L - hz1 \quad (15)$$

Figure 8:
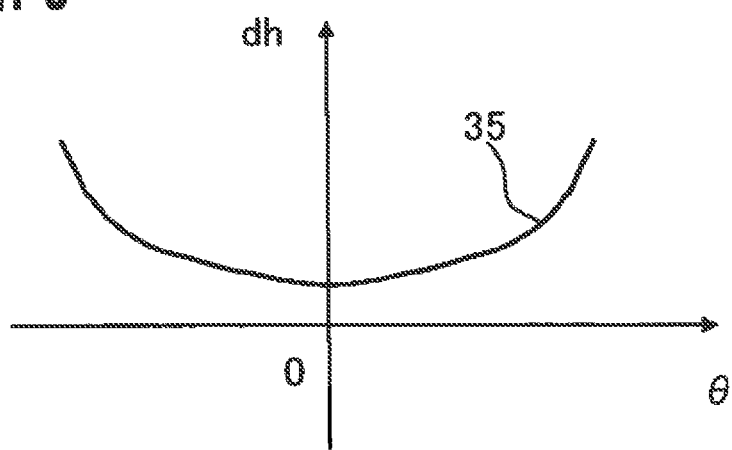
FIG. 8 is a graph representing a scanning-starting-point position characteristic utilized in a position calculation method according to Embodiment 3 of the present invention.

Through an experiment, the relationship between each scanning angle θ and the distance dh1 from the reference in the X-direction scanning electromagnet 5x to the scanning starting point 1x is given by a polynomial. Similarly, through an experiment, the relationship between each scanning angle θ and the distance dh2 from the reference in the Y-direction scanning electromagnet 5y to the scanning starting point 1y is given by a polynomial. The characteristic relationship between the distance dh and the scanning angle θ is represented, for example, by FIG. 8. FIG. 8 is a graph representing a scanning-starting-point position characteristic utilized in a position calculation method according to Embodiment 3 of the present invention. The abscissa denotes the scanning angle θ, and the ordinate denotes the distance dh from the reference in the scanning electromagnet 5 to the scanning starting point 1. A characteristic curve 35 is formed of plots of values obtained by the foregoing polynomial.

Figure 9:
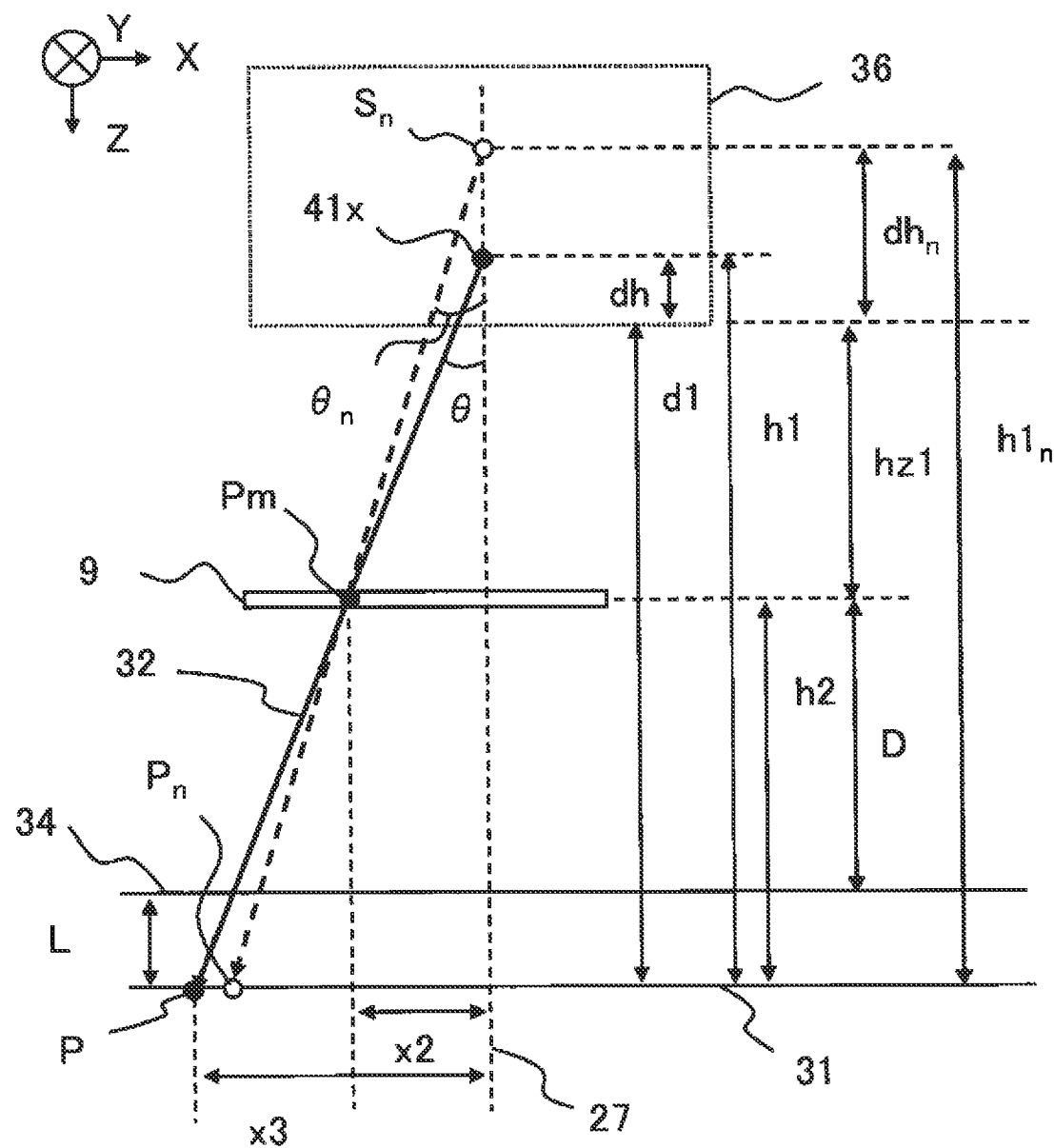
FIG. 9 is a diagram for explaining a position calculation method according to Embodiment 3 of the present invention.

With reference to FIG. 9, the position calculation method according to Embodiment 3 will be explained. FIG. 9 is a diagram for explaining a position calculation method according to Embodiment 3 of the present invention. In FIG. 9, a scanning starting point 41x is a real scanning starting point. The distance dh from the reference in the scanning electromagnet 5x to the scanning starting point 41x is the distance from the bottom of an iron core 36 of the scanning electromagnet 5x. The charged particle beam 2, scanned with the scanning angle θ at the scanning starting point 41x, passes through the beam position Pm (Xpm, Zpm) on the position monitor 9, and reaches the beam irradiation position P (Xp, Zp) for the diseased site of the patient 24. Similarly, the distance dh from the reference in the scanning electromagnet 5y to a scanning starting point 41y (a real scanning starting point in the Y-direction scanning electromagnet 5y) is the distance from the bottom of the iron core 36 of the scanning electromagnet 5y. The charged particle beam 2, scanned with the scanning angle θ at the scanning starting point 41y, passes through the beam position Pm (Ypm, Zpm) on the position monitor 9, and reaches the beam irradiation position P (Yp, Zp) for the diseased site of the patient 24.

In Embodiment 3, assuming that the charged particle beam 2, scanned at a scanning starting point candidate $S_n$ (Xs, $Zs_n$) which is a candidate for the scanning starting point, passes through the beam position Pm (Xpm, Zpm) and then reaches a beam irradiation position candidate $P_n$ ($Xp_n$, Zp) which is a candidate for the beam irradiation position, the scanning angle candidate $\theta_n$ which is a candidate for the scanning angle, is calculated in such a way that the scanning angle candidate $\theta_n$ is updated by use of the characteristic curve 35 until it converges. Here, n is an integer, and data with n signifies that the data is the n-th data. Reference characters $dh_n$ and $h1_n$ denote the distance from the reference in the scanning electromagnet 5 to the scanning starting point candidate $S_n$ and the distance (scanning starting point distance candidate information) from the scanning starting point candidate $S_n$ to the irradiation plane 31, respectively. The same manner is applied to the Y-direction. Assuming that the charged particle beam 2, scanned at the scanning starting point candidate $S_n$ (Ys, $Zs_n$), passes through the beam position Pm (Ypm, Zpm) and then reaches a beam irradiation position candidate $P_n$ ($Yp_n$, Zp), the scanning angle candidate $\theta_n$ is calculated in such a way that the scanning angle candidate $\theta_n$ is updated by use of the characteristic curve 35 until it converges.

AS the scanning starting point candidate $S_n$, for example, the scanning starting point 1x described in Embodiment 1 or the reference ($dh_n$=0) in the scanning electromagnet 5 can be utilized. At first, as the first step (Step S1, scanning angle calculation step), the scanning angle candidate $\theta_n$ is calculated from $h1_n$ and the length x2 from the center axis 27 to the beam position Pm. The scanning angle candidate $\theta_n$ can be given by the equation (16).

$$\theta_n = \tan^{-1}(x2/(h1_n - h2)) \quad (16)$$

Next, as the second step (Step S2), the distance $dh_n$ for the scanning angle candidate $\theta_n$ is calculated by use of the characteristic curve 35. AS the third step (Step 3, scanning starting point distance calculation step), the equation (17) is obtained by updating $h1_n$. Character $h1_{n+1}$ is an updated scanning starting point candidate information.

$$h1_{n+1} = dh_n + hz1 + D + L \quad (17)$$

Reference character d1 in FIG. 9 is the sum of hz1, D, and L (hz1+D+L).

As the fourth step (Step S4), $h1_{n+1}$ is substituted for $h1_n$ in the equation (16) so as to update the scanning angle candidate θn and obtain the scanning angle $\theta_{n+1}$. As the fifth step (Step S5), the absolute value E of $\theta_{n+1} - \theta_n$, is calculated and it is determined whether or not the absolute value E has become the same as or smaller than a predetermined value δ. In the case where the absolute value E has become the same as or smaller than a predetermined value δ, $h1_{n+1}$ at the time when $\theta_{n+1}$ is calculated is adopted as the distance h1 from the scanning starting point 41x to the beam irradiation position P for the diseased site of the patient 24. In the case where the absolute value E has not become the same as or smaller than a predetermined value δ, the process from the second step to the fifth step is repeated.

The position calculation method according to Embodiment 3 is implemented by the signal processing device 105 of the position calculation apparatus 30. There has been explained the X-direction length x3 from the center axis 27 to the beam irradiation position P; the Y-direction length y3 can also be calculated in the same manner. The polynomial expressing the scanning-starting-point position characteristic between each scanning angle θ and the distance dh1 from the reference in the X-direction scanning electromagnet 5x to the scanning starting point 1x and the polynomial expressing the scanning-starting-point position characteristic between each scanning angle θ and the distance dh2 from the reference in the Y-direction scanning electromagnet 5y to the scanning starting point 1y are stored in the memory of the signal processing device 105. When implementing the position calculation method according to Embodiment 3, the signal processing device 105 calculates the distance $dh_n$ by use of the polynomial stored in the memory.

In the position calculation method according to Embodiment 3, the relationship (scanning-starting-point position characteristic) between each scanning angle θ and the distance dh1 from the reference in the X-direction scanning electromagnet 5x to the scanning starting point 1x and the relationship (scanning-starting-point position characteristic) between each scanning angle θ and the distance dh2 from the reference in the Y-direction scanning electromagnet 5y to the scanning starting point 1y are preliminarily obtained, and then the calculation of the distance dh and the scanning angle θ is repeated by use of the scanning-starting-point position characteristics until the scanning angle θ converges; therefore, the fact that the scanning starting point changes depending on the scanning angle can be reflected in the calculation, and hence the beam irradiation position P (Xp, Yp) for the diseased site of the patient 24 can accurately be calculated in comparison with Embodiment 1. In the position calculation method according to Embodiment 3, the beam irradiation position P (Xp, Yp, Zp) for the diseased site of the patient 24 can accurately be calculated in comparison with Embodiment 1; therefore, the particle beam irradiation apparatus 58 and the particle beam therapy system 51 utilizing the position calculation method according to Embodiment 3 can more accurately irradiate a beam than those utilizing the position calculation method according to Embodiment 1.

In the position calculation method according to Embodiment 3, the beam irradiation position P (Xp, Yp, Zp) for the diseased site of the patient 24 can accurately be calculated by use of only the position monitor 9; therefore, in the particle beam irradiation apparatus 58 and the particle beam therapy system 51 utilizing the position calculation method according to Embodiment 3, the obstacle that causes scatter of the charged particle beam 2 can be diminished as much as possible, and the beam extracting window 7, the dose monitor 8, and the position monitor 9, which become the obstacles that cause the scatter of the charged particle beam 2, can be arranged at the downstream side. Thus, the beam size of the charged particle beam 2 can be reduced.

It can be said that the position calculation method according to Embodiment 3 is the one in which the information in the signal processing device 105 is utilized instead of the information on the position monitor 3 in the position calculation method according to Embodiment 2. Even in the case where the position calculation method according to Embodiment 2 is utilized, the fact that the scanning starting point changes depending on the scanning angle can also be reflected in the calculation; therefor, the beam irradiation position P (Xp, Yp) for the diseased site of the patient 24 can accurately be calculated in comparison with Embodiment 1.

Embodiment 4

In Embodiment 1, there has been described a case where the charged particle beam 2 vertically enters the scanning electromagnet 5 from the upstream side thereof; however, strictly speaking, in some cases, the charged particle beam 2 enters the scanning electromagnet 5 at a certain gradient. In Embodiment 4, the beam irradiation position P (Xp, Yp, Zp) for the diseased site of the patient 24 is calculated while considering the gradient of the angle at which the charged particle beam 2 enters the scanning electromagnet 5. As a result, the calculation accuracy can further be raised.

Figure 10:
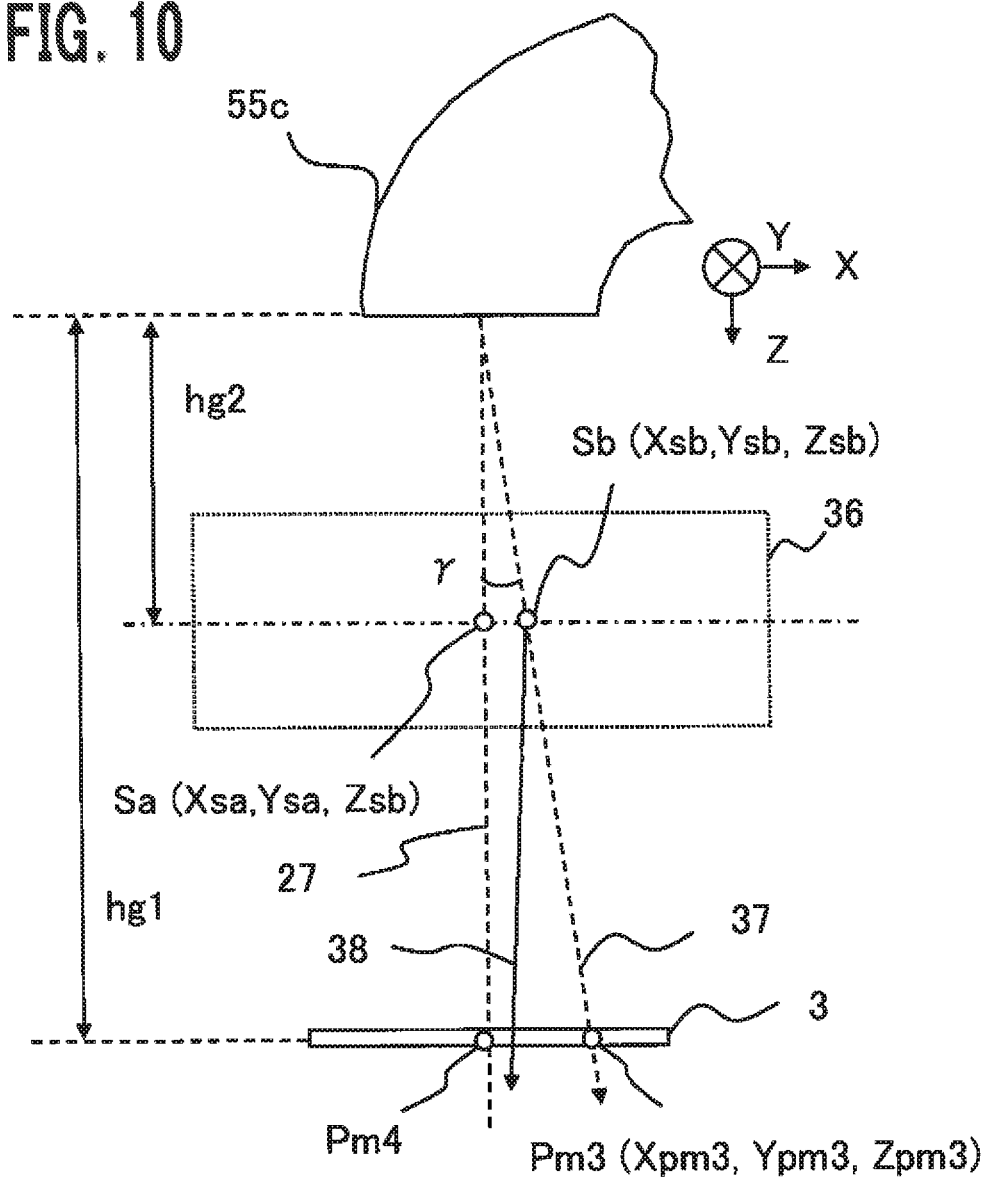
FIG. 10 is a diagram for explaining the scanning starting point in a position calculation method according to Embodiment 4 of the present invention.
Figure 11:
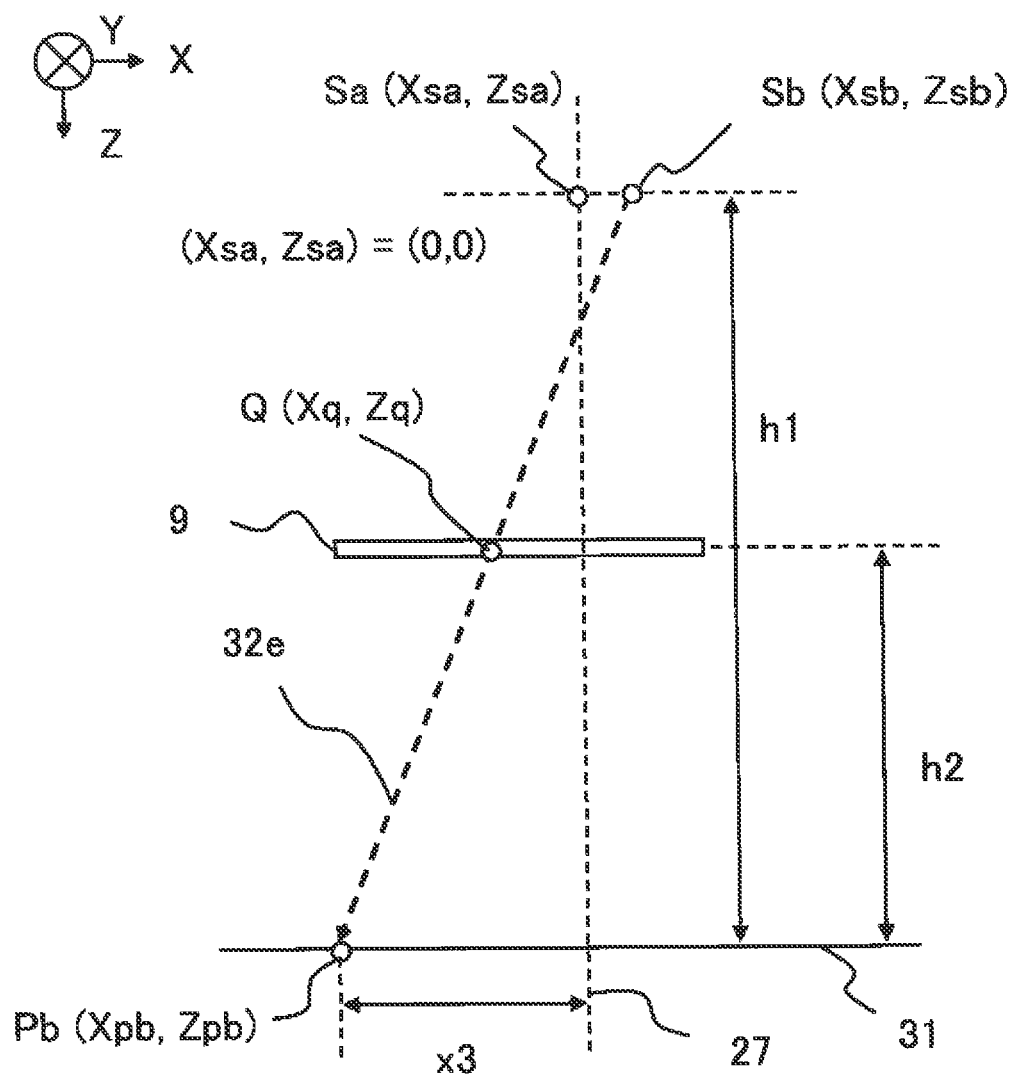
FIG. 11 is a diagram for explaining a position calculation method according to Embodiment 4 of the present invention.
Figure 12:
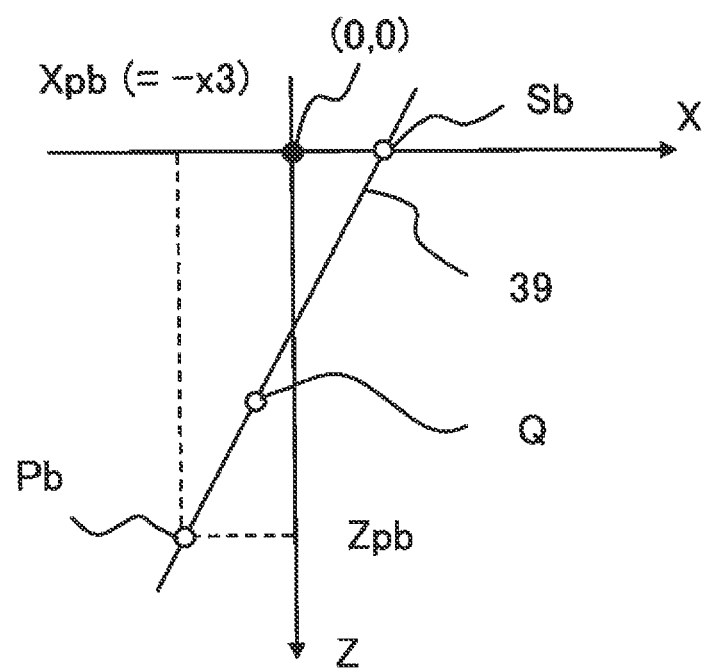
FIG. 12 is a diagram for explaining the characteristic line in a position calculation method according to Embodiment 4 of the present invention.

With reference to FIGS. 10 through 12, a position calculation method according to Embodiment 4 will be explained.

FIG. 10 is a diagram for explaining the scanning starting point in a position calculation method according to Embodiment 4 of the present invention. FIG. 11 is a diagram for explaining a position calculation method according to Embodiment 4 of the present invention; FIG. 12 is a diagram for explaining the characteristic line in a position calculation method according to Embodiment 4 of the present invention. As illustrated in FIG. 10, the charged particle beam 2 may enter the iron core 36 of the scanning electromagnet 5 from the deflection electromagnet 55c in an inclined manner by an angle of γ. This is because, for example, depending on the shape and structure of the building at the installation place of a particle beam therapy system, there may exist a case where the charged particle beam 2 is compelled to enter the scanning electromagnet 5 in an inclined manner by an angle of γ. Characters γx and γy denote the angle γ at which the charged particle beam 2 enters the iron core 36 of the X-direction scanning electromagnet 5x and the angle γ at which the charged particle beam 2 enters the iron core 36 of the Y-direction scanning electromagnet 5y, respectively. This is an example in which an actual scanning starting point Sb is situated at a position that is displaced from a scanning starting point Sa (Xsa, Ysa, Zsa) at the time when the charged particle beam 2 passes through the center axis 27. In this case, the charged particle beam 2, like an incident beam 37, enters the scanning electromagnet 5 and is scanned, like a deflection beam 38, from the scanning starting point Sb (Xsb, Ysb, Zsb) so as to be irradiated onto the diseased site of the patient 24.

In the position calculation method according to Embodiment 4, the beam irradiation position P (Xp, Yp, Zp) for the diseased site of the patient 24 is calculated by use of only the position monitor 9 when the charged particle beam 2 is irradiated in the therapy. Accordingly, the coordinates of the scanning starting point Sb is preliminarily obtained through an experiment by use of the position monitor 3. As illustrated in FIG. 10, the length hg1 from the position monitor 3 to the deflection electromagnet 55c is a known value inherent to the apparatus. Pm4 denotes the point at which the center axis 27 of the particle beam irradiation apparatus 58 passes through the position monitor 3. Pm3 (Xpm3, Ypm3, Zpm3) denotes the point at which the charged particle beam 2 passes through the position monitor 3 when the charged particle beam 2 is irradiated without controlling the scanning electromagnet 5. The angle γx at the X-direction scanning electromagnet 5x can be given by the equation (18) by use of |Xpm3| (the absolute value of Xpm3).

$$\gamma x = \tan^{-1}(|Xpm3|/hg1) \quad (18)$$

Similarly, the angle γy between the incident beam 37 and the center axis 27 at the Y-direction scanning electromagnet 5y can be given by the equation (19) by use of |Ypm3| (the absolute value of Ypm3).

$$\gamma y = \tan^{-1}(|Ypm3|/hg1) \quad (19)$$

For simplicity, it is assumed that the scanning starting point Sa is the Z-direction center point in the scanning electromagnet. The length hg2 from the scanning starting point Sa to the deflection electromagnet 55c is a known value inherent to the apparatus. Because in fact, the scanning starting point Sa in the X-direction scanning electromagnet 5x and the scanning starting point Sa in the Y-direction scanning electromagnet 5y are different from each other, the length hg2 at the X-direction scanning electromagnet 5x and the length hg2 at the Y-direction scanning electromagnet 5y are different from each other; however, the following explanation will be made by utilizing the same and a single reference character. Xsb can be calculated as hg2·tan γx, and Ysb can be calculated as hg2·tan γy.

As illustrated in FIG. 11, the charged particle beam 2, scanned at the scanning starting point Sb, passes through a point Q on the position monitor 9 and reaches the beam irradiation position Pb for the diseased site of the patient 24. FIG. 11 illustrates an example in which the X-direction length x3 from the center axis 27 in the X-direction scanning electromagnet 5x is calculated; with regard to the coordinates of the respective points, the Y coordinate is omitted, and only the X coordinate and the Z coordinate are expressed. As the origin coordinates (Xsa, Zsa)=(0, 0), the scanning starting point Sa that passes through the center axis 27 is adopted; the direction from Sa to Sb is the positive X direction, and the direction from Sa to the position monitor 9 is the positive Z direction. A trajectory 32e of the charged particle beam 2 is a straight line; three points, i.e., the scanning starting point Sb (Xsb, Zsb), the beam position Q (Xq, Zq) at the position monitor 9, and the beam irradiation position Pb (Xpb, Zpb) exist on the trajectory 32e.

At first, as the first step (Step S11), a characteristic line 39 that passes through the scanning starting point Sb and the beam position Q is obtained from the scanning starting point Sb (Xsb, Zsb) and the beam position Q (Xq, Zq). FIG. 12 represents the characteristic line 39. The characteristic line 39 can be given by the equation (20).

$$ax + bz + 1 = 0 \tag{20}$$

where a and b are constants. The constants a and b are substituted for those in the equation (20) with regard to the respective X and Z coordinates of Sb and Q; then, a and b can be calculated through the equation (21). The constants a and b can be expressed by use of an inverse matrix, as given by the equation (22).

$$\begin{pmatrix} Xsb & Zsb \\ Xq & Zq \end{pmatrix} \begin{pmatrix} a \\ b \end{pmatrix} = \begin{pmatrix} -1 \\ -1 \end{pmatrix} \tag{21}$$

$$\begin{pmatrix} a \\ b \end{pmatrix} = \begin{pmatrix} Xsb & Zsb \\ Xq & Zq \end{pmatrix}^{-1} \begin{pmatrix} -1 \\ -1 \end{pmatrix} \tag{22}$$

As the second step (Step S12), the coordinate Zpb of |Zpb| (the absolute value of the coordinates Zpb) that corresponds to the distance h1 from the scanning starting point Sb to the irradiation plane 31 is substituted for the equation (20) so that the coordinate Xpb is calculated. In the position calculation method according to Embodiment 4, the X coordinate (−x3) of the beam irradiation position Pb can directly be calculated without calculating the X-direction length x3 from the center axis 27 to the beam irradiation position Pb. In the case of FIG. 12, when Xpb is expressed by use of the X-direction length x3 of the beam irradiation position Pb, Xpb becomes −x3 because Xpb is negative.

The position calculation method according to Embodiment 4 is implemented by the signal processing device 105 of the position calculation apparatus 30. There has been explained about the X coordinate of the beam irradiation position P (Xp, Yp, Zp), i.e., the X coordinate of Pb with respect to the center axis 27 of the X-direction scanning electromagnet 5x; the Y coordinate of the beam irradiation position P (Xp, Yp, Zp) with respect to the center axis 27 of the Y-direction scanning electromagnet 5y can be calculated in the same manner. The polynomial expressing the energy Eb of the charged particle beam 2, the coordinates of the scanning starting point Sb for each energy Eb obtained through an experiment, and the characteristic line 39 is stored in the memory of the signal processing device 105. When implementing the position calculation method according to Embodiment 4, the signal processing device 105 calculates the beam irradiation position P (Xp, Yp, Zp) by use of the polynomial stored in the memory. Because the angle γ at the exit of the deflection electromagnet 55c differs depending on the energy Eb of the charged particle beam 2, the constants a and b of the polynomial change also depending on the energy Eb. In accordance with the energy Eb of the charged particle beam 2 to be irradiated, the beam irradiation position P (Xp, Yp, Zp) is calculated by use of the polynomial for which the constants a and b thereof corresponding to the energy Eb are selected.

In the position calculation method according to Embodiment 4, the beam irradiation position P (Xp, Yp, Zp) is calculated through a polynomial expressing the characteristic line 39 obtained based on the respective scanning starting point Sb (Xsb, Ysb, Zsb) in the X-direction scanning electromagnet 5x and the Y-direction scanning electromagnet 5y and the beam position Q (Xq, Yq, Zq) on the position monitor 9; therefore, even in the case where the charged particle beam 2 obliquely enters the scanning electromagnet 5x or 5y, the beam irradiation position P (Xp, Yp, Zp) for the diseased site of the patient 24 can accurately be calculated in comparison with the position calculation method according to Embodiment 1. In the position calculation method according to Embodiment 4, the beam irradiation position P (Xp, Yp, Zp) for the diseased site of the patient 24 can accurately be calculated in comparison with Embodiment 1; therefore, the particle beam irradiation apparatus and the particle beam therapy system 51 utilizing the position calculation method according to Embodiment 4 can more accurately irradiate a beam than those utilizing the position calculation method according to Embodiment 1.

In the position calculation method according to Embodiment 4, the beam irradiation position P (Xp, Yp, Zp) for the diseased site of the patient 24 can accurately be calculated by use of only the position monitor 9; therefore, in the particle beam irradiation apparatus 58 and the particle beam therapy system 51 utilizing the position calculation method according to Embodiment 4, the obstacle that causes scatter of the charged particle beam 2 can be diminished as much as possible, and the beam extracting window 7, the dose monitor 8, and the position monitor 9, which become the obstacles that cause the scatter of the charged particle beam 2, can be arranged at the downstream side. Thus, the beam size of the charged particle beam 2 can be reduced.

In position calculation method according to Embodiment 4, there has been described a case where the calculation is implemented under the assumption that the respective Z coordinates of the scanning starting point 1x of the X-direction scanning electromagnet 5x and the scanning starting point 1y of the Y-direction scanning electromagnet 5y are always fixed; however, the position calculation method according to Embodiment 4 can be combined with the position calculation method according to Embodiment 3. The combination with the position calculation method according to Embodiment 3 makes it possible to consider the shift of the scanning starting point, caused by the angle at which the charged particle beam 2 enters the scanning starting electromagnet 5x or 5y and the scanning angle; therefore, the beam irradiation position P (Xp, Yp, Zp) for the diseased site of the patient 24 can further accurately be calculated. Thus, the particle beam irradiation apparatus 58 and the particle beam therapy system 51 utilizing the position calculation method in which the foregoing two parameters are taken into consideration can more accurately irradiate a beam.

It can be said that the position calculation method according to Embodiment 4 is the one in which the information in the position calculation apparatus 30 is utilized instead of the information on the position monitor 3 in the position calculation method according to Embodiment 2. Even in the case where the position calculation method according to Embodiment 2 is utilized, the fact that the scanning starting point changes depending on the angle at which the charged particle beam 2 enters the scanning electromagnet 5x or 5y can also be reflected in the calculation; therefor, the beam irradiation position P (Xp, Yp) for the diseased site of the patient 24 can accurately be calculated in comparison with the position calculation method according to Embodiment 1.

In Embodiment 1, the distance sensor 22 has been explained as an encoder that detects the rotation of the motor 15 in the duct driving device 12; however, there may be utilized an ampere meter for a current that flows in a variable resistor connected in such a way that the value thereof changes in accordance with the position of the vacuum duct 6. The distance sensor 22 can be applied also to Embodiments 2 through 4.

In Embodiments 1 through 4, there has been explained a case where due to movement of the position monitor 9, the relative positions of the scanning electromagnet and the position monitor change; however, the present invention is not limited thereto and can also be applied to a case where due to movement of the scanning electromagnet, the relative positions of the scanning electromagnet and the position monitor change. In addition, in Embodiments 1 through 4, there has been explained an example of spot scanning where the charged particle beam 2 stops for each irradiation spot; however, the present invention is not limited thereto and can also be applied to other scanning irradiation methods such as an irradiation method in which the charged particle beam 2 is stopped when slices are changed and the charged particle beam 2 is continuously irradiated when irradiation is performed within a single and the same slice and a raster scanning.

DESCRIPTION OF REFERENCE NUMERALS

1x, 1y: scanning starting point
2: charged particle beam
3: position monitor
5, 5x, 5y: scanning electromagnet
6: vacuum duct
7: beam extracting window
9: position monitor
23: irradiation control apparatus
25: irradiation subject
27: center axis (beam axis)
30: position calculation apparatus
31: irradiation plane
41x: scanning starting point
35: characteristic curve (scanning-starting-point position characteristic)
51: particle beam therapy system
54: accelerator
58, 58a, 58b: particle beam irradiation apparatus
59: beam transport system
D: distance from reference point (skin surface) to position monitor
Sa, Sb: scanning starting point
Pm, Pm1, Pm2: beam position
P: beam irradiation position
θ: scanning angle
$θ_n$, $θ_{n+1}$: scanning angle candidate
$S_n$: scanning starting point candidate
$h1_n$: scanning starting point distance candidate information
$h1_{n+1}$: updated scanning starting point candidate information

The invention claimed is:

1. A particle beam irradiation apparatus that irradiates a charged particle beam accelerated by an accelerator onto an irradiation subject, the particle beam irradiation apparatus comprising:
a scanning electromagnet configured to scan the charged particle beam in a direction that is perpendicular to a beam axis;
a position monitor that (i) is disposed such that the relative position thereof to the scanning electromagnet in the beam axis direction is changeable to a desired position and (ii) is configured to detect a passing position of the charged particle beam;
a distance sensor configured to detect a changing beam-axis direction position of the position monitor from at least a first beam-axis direction position to at least a second beam axis direction position when irradiation is performed onto the irradiation subject; and
an irradiation control apparatus configured to
calculate, based on a signal received from the distance sensor regarding the changing beam-axis direction position information of the position monitor, position monitor distance information, which includes a beam-axis-direction distance from an irradiation plane on the irradiation subject to the position monitor,
calculate a beam irradiation position on the irradiation subject, based on (i) a detection signal, including information on the passing position of the charged particle beam, from the position monitor and (ii) the calculated position monitor distance information, which includes information on a changed beam-axis direction position of the position monitor, and
control irradiation of the charged particle beam, wherein
the irradiation control apparatus includes a position calculation apparatus configured to calculate the beam irradiation position, on the irradiation plane, that is expressed based on a distance from an intersection point of the beam axis with the irradiation plane, said position calculation apparatus calculates the beam irradiation position based on (i) a beam position detected by the position monitor, (ii) scanning starting point distance information that includes a distance from the irradiation plane of the irradiation subject to a scanning starting point, of the charged particle beam, in the scanning electromagnet, and (iii) the position monitor distance information, which includes information on a changed beam-axis direction position of the position monitor.

2. The particle beam irradiation apparatus according to claim 1,
wherein the position calculation apparatus includes a memory that stores (i) a scanning-starting-point position characteristic that is a characteristic between a scanning angle θ, which is the angle between the trajectory of the charged particle beam scanned by the scanning electromagnet and the beam axis, and (ii) a distance dh from an arbitrarily determined reference point in the scanning electromagnet to the scanning starting point;
wherein, based on a beam position detected by the position monitor and a scanning starting point distance candidate information h1 n on a distance from the irradiation plane of the irradiation subject to a scanning starting point candidate Sn, which is a candidate for the scanning starting point, the position calculation apparatus is configured to implement a scanning angle calculation step in which a scanning angle candidate θn, which is a candidate for the scanning angle θ, is calculated;
wherein the position calculation apparatus is further configured to implement a scanning starting point distance calculation step in which an updated scanning starting point distance candidate information h1n+1 including a distance dhn, which is a candidate for the distance dh, is calculated based on the scanning angle candidate θn and the scanning-starting-point position characteristic;
wherein the position calculation apparatus is further configured to repeat the scanning angle calculation step and the scanning starting point distance calculation step until a scanning angle difference between the scanning angle candidate θn and the scanning angle candidate θn+1 is calculated by implementing the scanning angle calculation step, based on the updated scanning starting point distance candidate information h1n+1; and wherein the position calculation apparatus is further configured to calculate the beam irradiation position on the irradiation plane, that is expressed based on a distance from the intersection point of the beam axis with the irradiation plane, by adopting the updated scanning starting point distance candidate information h1n+1 at a time when the scanning angle difference has become the same as or smaller than the predetermined value, as the scanning starting point distance information on a distance from the irradiation plane of the irradiation subject to the scanning starting point, of the charged particle beam, in the scanning electromagnet.

3. The particle beam irradiation apparatus according to claim 1, wherein the position calculation apparatus is configured to calculate:

a characteristic equation expressing a straight line that passes through (i) preliminarily measured position coordinates of the scanning starting point in the scanning electromagnet and (ii) the coordinates of the beam position detected by the position monitor, and the beam irradiation position on the irradiation plane, based on the characteristic equation.

4. The particle beam irradiation apparatus according to claim 3, wherein the position coordinates of the scanning starting point in the scanning electromagnet is calculated based on a gradient angle that is the angle between the beam axis and an incident axis along which the charged particle beam enters the scanning electromagnet.

5. The particle beam irradiation apparatus according to claim 1, further comprising:

an upstream-side position monitor that is situated at the upstream side of the position monitor and disposed such that the relative position thereof to the scanning electromagnet in the beam axis direction is fixed, said upstream-side position monitor being configured to detect a passing position of the charged particle beam, wherein the position calculation apparatus is configured to calculate the beam irradiation position on the irradiation plane, that is expressed based on a distance from the intersection point of the beam axis with the irradiation plane, based on (i) a first beam position detected by the upstream-side position monitor and (ii) a second beam position detected by the position monitor, the scanning starting point distance information on a distance from the irradiation plane of the irradiation subject to the scanning starting point, of the charged particle beam, in the scanning electromagnet, an upstream-side position monitor distance information on a distance from the irradiation plane of the irradiation subject to the upstream-side position monitor, and the position monitor distance information.

6. The particle beam irradiation apparatus according to claim 1, further comprising:

a driving device configured to change beam-axis-direction relative positions of the scanning electromagnet and the position monitor, wherein the position monitor is disposed at the downstream side of a beam extracting window for extracting the charged particle beam from a vacuum duct, which ensures a vacuum region through which the charged particle beam is transported, toward the irradiation subject.

7. A particle beam therapy system comprising:

a beam generation apparatus configured to generate a charged particle beam and accelerate the charged particle beam by means of an accelerator;

a beam transport system configured to transport the charged particle beam accelerated by the accelerator; and the particle beam irradiation apparatus of claim 1, which is configured to irradiate the charged particle beam transported by the beam transport system onto an irradiation subject.

8. The particle beam irradiation apparatus according to claim 1, wherein the distance sensor detects the changing beam-axis direction position of the position monitor by detecting a beam-axis-direction distance from a reference point that is arbitrarily determined in the beam-axis direction to the position monitor, and wherein the position calculation apparatus calculates the position monitor distance information, based on the beam-axis-direction position information, on the position monitor, that is calculated from the signal detected by the distance sensor and a distance from the arbitrarily determined reference point to the irradiation plane on the irradiation subject.

* * * * *